United States Patent

Bourzat et al.

[11] Patent Number: 5,475,106
[45] Date of Patent: * Dec. 12, 1995

[54] N-PHENYLGLYCINAMIDE CCK ANTAGONISTS AND PHARMACEUTICAL COMPOSITIONS CONTAINING THEM

[75] Inventors: Jean-Dominique Bourzat, Vincennes; Marc Capet, Thiais; Claude Cotrel, Paris; Claude Guyon, Saint Maur Des Fosses; Franco Manfre, Vitry Sur Seine; Gérard Roussel, Soisy Sur Seine, all of France

[73] Assignee: Rhone-Poulenc Rorer S.A., Antony, France

[ * ] Notice: The portion of the term of this patent subsequent to Dec. 20, 2011, has been disclaimed.

[21] Appl. No.: 924,065

[22] PCT Filed: Mar. 5, 1991

[86] PCT No.: PCT/FR91/00174

§ 371 Date: Oct. 8, 1992

§ 102(e) Date: Oct. 8, 1992

[87] PCT Pub. No.: WO91/13907

PCT Pub. Date: Sep. 19, 1991

[30] Foreign Application Priority Data

Mar. 7, 1990 [FR] France ................... 90 02889
Oct. 16, 1990 [FR] France ................... 90 12727

[51] Int. Cl.$^6$ ............ C07K 5/06; A61K 31/325; C07C 229/00; C07C 205/00
[52] U.S. Cl. ............ 544/58.4; 544/58.5; 546/168; 546/194; 548/253; 548/334.1; 548/545; 560/9; 560/21; 560/22; 560/34; 560/39; 560/41
[58] Field of Search ............ 560/34, 22, 9, 560/21, 39, 41; 514/542, 539, 227.5, 311, 317, 381, 399, 424; 546/168, 194; 544/58.4, 58.5; 548/253, 334.1, 525

[56] References Cited

U.S. PATENT DOCUMENTS

| | | | |
|---|---|---|---|
| 3,515,744 | 6/1970 | Steinbrunn et al. | 560/34 |
| 4,055,414 | 10/1977 | Chupp | 560/22 X |
| 4,377,587 | 3/1983 | Hubele et al. | 424/269 |
| 4,442,117 | 4/1984 | Kunz et al. | 424/273 R |
| 4,448,773 | 5/1984 | Ribbli et al. | 424/211 |
| 4,492,683 | 1/1985 | Nagpal | 424/309 |
| 4,610,985 | 9/1986 | Fuhrer et al. | 514/235 |
| 5,324,747 | 6/1994 | Carson et al. | 514/533 |
| 5,338,760 | 8/1994 | Bourzat et al. | 514/539 |
| 5,374,656 | 12/1994 | Bourzat et al. | 514/542 |

FOREIGN PATENT DOCUMENTS

| | | | |
|---|---|---|---|
| 166355 | 1/1986 | European Pat. Off. | 560/22 |
| 175498 | 3/1986 | European Pat. Off. | 560/22 |
| 397556 | 11/1990 | European Pat. Off. | 560/22 |
| 91-13862 | 9/1991 | WIPO | 560/34 |

Primary Examiner—Floyd D. Higel
Attorney, Agent, or Firm—Finnegan, Henderson, Farabow, Garrett & Dunner

[57] ABSTRACT

Compounds of formula:

$$\begin{array}{c} \text{CH}(R_1)-\text{CO}-R_2 \\ | \\ R_4-\text{N}-\text{CO}-\text{CH}_2-\text{NH}-\text{CO}-R_3 \end{array} \quad (I)$$

in which $R_1$ represents a hydrogen atom, an alkyl or alkoxycarbonyl radical or a phenyl radical, optionally substituted, $R_2$ represents an alkoxy, optionally substituted cycloalkyloxy, cycloalkylalkyloxy, phenylalkyloxy, polyfluoroalkyloxy or cinnamyloxy radical or a radical —$NR_5R_6$, $R_3$ represents a phenylamino radical in which the phenyl ring is optionally substituted, an optionally substituted phenyl radical or a naphthyl, indolyl or quinolyl radical, $R_4$ represents a substituted phenyl radical, $R_5$ and $R_6$, which may be identical or different, represent a hydrogen atom or an alkyl, optionally substituted phenyl, indanyl, cycloalkylalkyl, cycloalkyl or phenylalkyl radical, or alternatively $R_5$ and $R_6$, together with the nitrogen atom to which they are attached, form a heterocycle, their preparation and medicinal products containing them.

9 Claims, No Drawings

N-PHENYLGLYCINAMIDE CCK ANTAGONISTS AND PHARMACEUTICAL COMPOSITIONS CONTAINING THEM

The present invention relates to N-phenylglycinamide derivatives of formula:

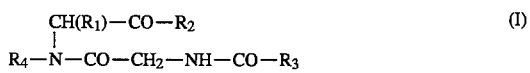

to their preparation and to medicinal products containing them.

In the formula (I), $R_1$ represents a hydrogen atom, an alkyl or alkoxycarbonyl radical or a phenyl radical (optionally substituted with one or more substituents selected from halogen atoms and alkyl, alkoxy, alkylthio, nitro and amino radicals), $R_2$ represents an alkoxy, cycloalkyloxy (optionally substituted with at least one alkyl radical), cycloalkylalkyloxy, phenylalkyloxy, polyfluoroalkyloxy or cinnamyloxy radical or a radical —$NR_5R_6$, $R_3$ represents a phenylamino (in which the phenyl ring is optionally substituted with one or more substituents selected from halogen atoms and alkyl, alkoxy, alkylthio, carboxyl, hydroxyl, mono- or polyhydroxyalkyl, nitro, amino, acyl, cyano, sulphamoyl, carbamoyl, benzoyl, trifluoromethylsulphonamido, alkoxycarbonyl, phenylhydroxymethyl, piperidino, hydroxyiminoalkyl, alkoxyiminoalkyl, alkylsulphinyl, hydroxyaminocarbonyl, alkoxyaminocarbonyl, 5-tetrazolyl, 5-tetrazolylalkyl, sulpho, —alk—O—CO—alk, —alk—O—alk, —alk—COOX, —O—alk—COOX, —alk'—COOX, —CH═CH—COOX, —CO—COOX, —alk—$SO_3H$, —CH═CH—alk', —C(═NOH)—COOX and —S—alk—COOX radicals), phenyl (optionally substituted with one or more substituents selected from halogen atoms and alkyl, alkoxy and alkylthio radicals), naphthyl, indolyl or quinolyl radicals, $R_4$ represents a phenyl radical substituted with one or more substituents selected from halogen atoms, alkyl, alkoxy, hydroxyl, polyfluoroalkyl, nitro, alkylthio, alkoxycarbonyl, carboxyl, acylamino, methylenedioxy, polyfluoroalkoxy, trifluoromethylthio, phenoxy, phenyl, benzyl and phenylamino radicals and a radical —CO—$NR_5R_6$, $R_5$ and $R_6$, which may be identical or different, represent a hydrogen atom or an alkyl, phenyl (optionally substituted with one or more substituents selected from halogen atoms and alkyl, alkoxy and alkylthio radicals), indanyl, cycloalkylalkyl, cycloalkyl or phenylalkyl radicals, or alternatively $R_5$ and $R_6$, together with the nitrogen atom to which they are attached, form a saturated or unsaturated mono- or polycyclic heterocycle containing 4 to 9 carbon atoms and one or more hetero atoms (O, N, S) and optionally substituted with one or more alkyl, alkoxy, alkoxycarbonyl, dialkylcarbamoyl or phenyl radicals or, in combination with a carbon atom of the heterocycle, optionally substituted with a 4- or 5-membered spiromonocyclic ring-system optionally containing one or more hetero atoms (O, S, N), alk represents an alkyl or alkylene radical, alk' represents a hydroxyalkylene or hydroxyalkyl radical, X represents a hydrogen atom or an alkyl radical.

In the foregoing definitions and those which will be mentioned below, except where otherwise stated, the alkyl, alkylene and alkoxy radicals and alkyl, alkylene and alkoxy portions contain 1 to 4 carbon atoms in a straight or branched chain, cycloalkyl radicals and portions contain 3 to 6 carbon atoms and the acyl radicals contain 2 to 4 carbon atoms.

In the formula (I), the halogen atoms are preferably chlorine, bromine and fluorine atoms.

When $R_5$ and $R_6$, together with the nitrogen atom to which they are attached, form a heterocycle, the latter is preferably a piperidino ring (optionally substituted with at least one alkyl, phenyl, alkoxycarbonyl or dialkylcarbamoyl radical) or a perhydro-1-azepinyl, 1-indolinyl, 1,2,3,6-tetrahydro-1pyridyl, 1,2,3,4-tetrahydro-1-quinolyl, 1-pyrrolidinyl, 3,4-dihydro-2H-1,4-benzoxazin-4-yl, 3,4-dihydro-2H-1,4-benzothiazin- 4-yl, N-alkyl-1,2,3,4-tetrahydro-1-quinoxalinyl, perhydro-1-quinolyl, 1,2,3,4-tetrahydro-2-isoquinolyl, 8-azaspiro[4.5]decan-8-yl, 8-aza-1,4-dioxaspiro[ 4.5]decan-8-yl, 2- or 3-phenyl-1-pyrrolidinyl or thiomorpholino (optionally substituted with at least one alkyl radical) ring-system.

The compounds of formula (I) containing one or more asymmetric centers possess isomeric forms. The racemates and enantiomers of these compounds also form part of the invention.

The compounds of formula (I) for which $R_3$ represents a phenylamino radical (in which the phenyl ring is optionally substituted with one or more substituents selected from halogen atoms and alkyl, alkoxy, alkylthio, nitro, acyl, cyano, sulphamoyl, benzoyl, alkoxycarbonyl, —alk—O—alk, 5-tetrazolyl and 5-tetrazolylalkyl radicals) may be obtained by the action of an isocyanate of formula:

in which $R_9$ represents a phenyl radical (optionally substituted with one or more substituents selected from halogen atoms and alkyl, alkoxy, alkylthio, nitro, acyl, cyano, sulphamoyl, benzoyl, alkoxycarbonyl, —alk—O—alk, 5-tetrazolyl and 5-tetrazolylalkyl radicals) on an amino derivative of formula:

in which $R_1$, $R_2$ and $R_4$ have the same meanings as in the formula (I).

This reaction is generally performed in an inert solvent such as tetrahydrofuran, dimethylformamide, a chlorinated solvent (e.g. chloroform, 1,2-dichloroethane) or an aromatic solvent (e.g. benzene, toluene), at a temperature between 10° C. and the boiling point of the solvent.

The isocyanates of formula (II) are commercially available or may be obtained by application or adaptation of the method described by R. RICHTER et al., The Chemistry of Cyanates and their thio derivatives, S. PATAI, part 2, Wiley New York (1977).

The derivatives of formula (III) may be obtained by application or adaptation of the method described in the examples or of the method described by T. WIELAND et al., Justus Liebigs Ann. Chem., 613, 84 (1958) or by adaptation of GABRIEL's method (GIBSON et al., Angew Chem. Int. Ed., 7, 919 (1968)) which consists in reacting a hydrazine of formula:

in which $R_{10}$ represents a hydrogen atom or a methyl radical, with a derivative of formula:

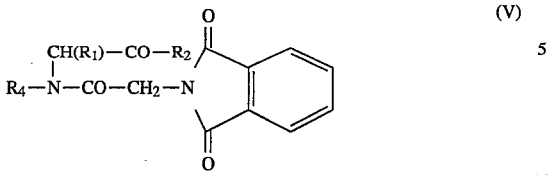

in which $R_1$, $R_2$ and $R_4$ have the same meanings as in the formula (I).

This reaction is preferably performed in an inert solvent such as an alcohol (e.g. methanol, ethanol) or a chlorinated solvent (e.g. dichloromethane, chloroform), at a temperature between 0° C. and the boiling point of the solvent.

The derivatives of formula (V) may be obtained by the action of an amine of formula:

$$R_4-NH-CH(R_1)-CO-R_2 \quad (VI)$$

in which $R_1$, $R_2$ and $R_4$ have the same meanings as in the formula (I), on 2-phthalimidoacetyl chloride.

This reaction is generally performed in an inert solvent (e.g. chloroform, 1,2-dichloroethane), in the presence of a base such as a tertiary amine, e.g. a trialkylamine, or an alkali metal carbonate or bicarbonate, at a temperature in the region of 20° C.

2-Phthalimidoacetyl chloride may be prepared by application of the method described by W. GRASSMAN et al., Chem. Ber., 83, 244 (1950).

The amines of formula (VI) may be obtained by the action of an amino derivative of formula:

$$R_4-NH_2 \quad (VII)$$

in which $R_1$ has the same meanings as in the formula (I), on a halogenated derivative of formula:

$$Hal-CH(R_1)-CO-R_2 \quad (VIII)$$

in which $R_1$ and $R_2$ have the same meanings as in the formula (I) and Hal represents a halogen atom (preferably chlorine or bromine).

This reaction is generally performed in an inert solvent such as acetonitrile, dimethylformamide, tetrahydrofuran or a chlorinated solvent, optionally in the presence of a base such as an alkali metal hydride or alkali metal bicarbonate, at the boiling point of the solvent.

The substituted anilines of formula (VII) may be obtained by application or adaptation of the method described by R. SCHRÖTER, Methoden der Organischen Chemie, Houben Weil, Volume XI/1, p. 360.

The halogenated derivatives of formula (VIII) may be obtained by halogenation of a derivative of formula:

$$HCH(R_1)-CO-R_2 \quad (IX)$$

in which $R_1$ and $R_2$ have the same meanings as in the formula (I).

This reaction is generally performed by means of bromine or chlorine, optionally in the presence of acetamide.

The derivatives of formula (IX) for which $R_2$ represents an alkoxy, optionally substituted cycloalkyloxy, cycloalkylalkoxy, phenylalkyloxy, polyfluoroalkyloxy or cinnamyloxy radical may be obtained by esterification of an acid of formula:

$$HCH(R_1)-COOH \quad (X)$$

in which $R_1$ has the same meanings as in the formula (I).

This esterification is performed by any method known to those skilled in the art for converting an acid to an ester. It is possible, e.g., to react the corresponding alcohol in the presence of an acid such as sulphuric acid.

The acids of formula (X) for which $R_1$ represents an alkoxycarbonyl radical may be obtained by application or adaptation of the method described in Acta. Chem. Scand., B29, 687 (1975).

The derivatives of formula (IX) for which $R_2$ represents a radical $-NR_5R_6$ may be obtained by the action of an acid of formula (X), or a reactive derivative of this acid, on an amine of formula:

$$HNR_5R_6 \quad (XI)$$

in which $R_5$ and $R_6$ have the same meanings as in the formula (I).

When the acid is employed, the reaction is performed in the presence of a peptide-condensing agent such as a carbodiimide (e.g. dicyclohexylcarbodiimide) or N,N'-carbonyldiimidazole, in an inert solvent such as an ether (e.g. tetrahydrofuran, dioxane), an amide (e.g. dimethylformamide) or a chlorinated solvent (e.g. methylene chloride, 1,2-dichloroethane, chloroform), at a temperature between 0° C. and the refluxing temperature of the reaction mixture.

When a reactive derivative of the acid is employed, it is possible to react the acid anhydride, a mixed acid anhydride or an acid halide, or an ester (which may be selected from activated or unactivated esters of the acid).

The reaction is then performed either in an organic medium, optionally in the presence of an acceptor for acid such as a nitrogenous organic base (e.g. trialkylamine, pyridine, 1,8-diazabicyclo-[ 5.4.0]undec-7-ene or 1,5-diazabicyclo[4.3.0] -non-5-ene), in a solvent such as is mentioned above or a mixture of these solvents, at a temperature between 0° C. and the refluxing temperature of the reaction mixture, or in a two-phase aqueous-organic medium in the presence of an alkali metal or alkaline earth metal base (sodium hydroxide, potassium hydroxide) or alkali metal or alkaline earth metal carbonate or bicarbonate, at a temperature of between 0° and 40° C.

The derivatives of formula (V) may also be obtained by the action of a derivative of formula (VIII) on a derivative of formula:

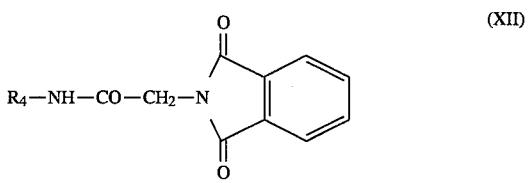

in which $R_4$ has the same meanings as in the formula (I).

This reaction is generally performed in an inert solvent such as acetonitrile, dimethylformamide or tetrahydrofuran, in the presence of a base such as an alkali metal hydride or alkali metal or alkaline earth metal carbonate or bicarbonate, at a temperature between 15° C. and the refluxing temperature of the reaction medium.

The derivatives of formula (XII) may be obtained by the action of an amine of formula (VII) on 2-phthalimidoacetyl chloride.

This reaction is generally performed in an inert solvent such as a chlorinated solvent (e.g. chloroform, 1,2-dichloroethane), in the presence of a base such as a tertiary amine, e.g. triethylamine, at a temperature in the region of 20° C.

The derivatives of formula (V) may also be obtained by the action of phthalimide potassium salt on a derivative of formula:

(XIII)

in which $R_1$, $R_2$ and $R_4$ have the same meanings as in the formula (I).

This reaction is performed in an inert solvent such as dimethylformamide, at a temperature in the region of 100° C.

The derivatives of formula (XIII) may be obtained by the action of an amine of formula (VI) on chloroacetyl chloride.

This reaction is performed in an inert solvent such as dimethylformamide, tetrahydrofuran or a chlorinated solvent, in the presence of a tertiary amine such as triethylamine, at a temperature of between 10° C. and 80° C.

The derivatives of formula (V) for which $R_2$ represents a radical —$NR_5R_6$ may also be obtained by the action of an amine of formula (XI) on an acid of formula:

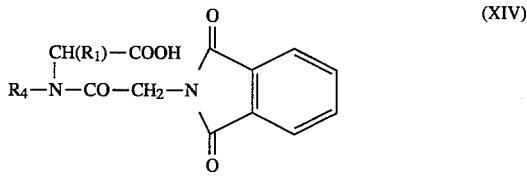

(XIV)

in which $R_1$ and $R_4$ have the same meanings as in the formula (I), or a reactive derivative of this acid.

This reaction is generally performed under the conditions mentioned above for the reaction of the acids of formula (X) and the amines of formula (XI).

The acids of formula (XIV) may be obtained by hydrolysis of the corresponding esters.

This hydrolysis is performed by any method known to those skilled in the art enabling an ester to be converted to an acid. Preferably, trifluoroacetic acid is used, at a temperature in the region of 20° C.

The derivatives of formula (V) for which $R_4$ represents a phenyl radical substituted with a hydroxyl radical may also be obtained by dealkylation of the corresponding derivatives for which $R_4$ represents a phenyl radical substituted with an alkoxy radical.

This dealkylation is preferably performed by means of boron tribromide, in an inert solvent such as a chlorinated solvent, at a temperature in the region of 20° C.

The derivatives of formula (V) for which $R_4$ represents a phenyl radical substituted with an alkoxy radical may also be obtained by the action of an alkylating agent such as an alkyl halide on the corresponding derivatives for which $R_4$ represents a phenyl radical substituted with a hydroxyl radical.

This reaction is preferably performed by means of sodium hydride in an inert organic solvent such as dimethylformamide, at a temperature of between 10° C. and 50° C.

The compounds of formula (I) for which $R_3$ represents a phenylamino radical (in which the phenyl ring is optionally substituted with one or more substituents selected from halogen atoms and alkyl, alkoxy, alkylthio, nitro, acyl, cyano, sulphamoyl, benzoyl, alkoxycarbonyl, 5-tetrazolyl, 5-tetrazolylalkyl, trifluoromethylsulphonamido and —alk—O—alk radicals [lacuna] may also be prepared by the action of an amine of formula (VI) on an acid of formula:

(XV)

in which $R_3$ has the same meanings as above, or a reactive derivative of this acid.

This reaction is generally performed under the conditions mentioned above for the reaction of the acids of the formula (X) with an amine of formula (XI).

The acids of formula (XV) may be obtained by the action of an isocyanate of formula (II) on glycine.

This reaction is generally performed in aqueous solution, in the presence of a base such as an alkali metal bicarbonate, at a temperature in the region of 20° C.

The compounds of formula (I) for which $R_3$ represents an optionally substituted phenylamino radical may also be prepared by the action of a derivative of formula:

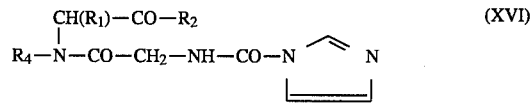

(XVI)

in which $R_1$, $R_2$ and $R_4$ have the same meanings as in the formula (I), on a derivative of formula:

(XVII)

in which $R_{11}$ represents a phenyl radical (optionally substituted with one or more substituents selected from halogen atoms and alkyl, alkoxy, alkylthio, carboxyl, hydroxyl, mono- or polyhydroxyalkyl, nitro, amino, acyl, cyano, sulphamoyl, carbamoyl, benzoyl, alkoxycarbonyl, trifluoromethylsulphonamido, hydroxyaminocarbonyl, alkoxyaminocarbonyl, 5-tetrazolyl, 5-tetrazolylalkyl, phenylhydroxymethyl, piperidino, hydroxyiminoalkyl, alkoxyiminoalkyl, alkylsulphinyl, sulpho, —alk—O—CO—alk, —alk—O—alk, —alk—COOX, —O—alk—COOX, —alk'—COOX, —CH=CH—COOX, —CO—COOX, —alk—$SO_3H$, —CH=CH—alk', —C(=NOH)—COOX and —S—alk—COOX radicals [lacuna].

This reaction is generally performed in an inert solvent such as tetrahydrofuran, dimethylformamide, a chlorinated solvent or an aromatic solvent, at a temperature between 20° C. and the boiling point of the solvent.

The substituted anilines of formula (XVII) may be obtained by application or adaptation of the methods described by R. SCHRÖTER, Methoden der Organischen Chemie, Houber Weil, Volume XI/1, p. 360; G. J. ESSELEN et al., J. Am. Chem. Soc., 36, 322 (1914); G. ADRIANT et al., Bull. Soc. Chim. Fr, 1511 (1970); W. A. JACOBS et al., J. Am. Chem. Soc. 39, 2438 (1917); and J. Am. Chem. Soc., 39, 1438 (1917); and in the examples.

The derivatives of formula (XVI) may be obtained by the action of a derivative of formula (III) on N,N-carbonyldiimidazole.

This reaction is generally performed in an inert solvent such as tetrahydrofuran, dimethylformamide, a chlorinated solvent or an aromatic solvent, at a temperature between 20° C. and the boiling point of the solvent.

The compounds of formula (I) for which $R_3$ represents a phenylamino radical in which the phenyl ring is optionally substituted may also be prepared by the action of an amine of formula (XVII) on an isocyanate of formula:

(XVIII)

in which $R_1$, $R_2$ and $R_4$ have the same meanings as in the formula (I).

This reaction is generally performed in an inert solvent such as an ether (e.g. tetrahydrofuran), a chlorinated solvent (e.g. chloroform, methylene chloride) or an aromatic solvent (e.g. benzene, toluene), at a temperature between 10° C. and the boiling point of the solvent.

The isocyanates of formula (XVIII) may be obtained by the action of an amine of formula (VI) on isocyanatoacetyl chloride.

This reaction is performed in an inert solvent such as ether (e.g. diethyl ether), in the presence of a nitrogenous organic base such as a trialkylamine or pyridine, at a temperature in the region of 20° C.

The compounds of formula (I) for which $R_3$ represents a phenylamino radical in which the phenyl ring is substituted with at least one carboxyl, —alk—COOH, —O—alk—COOH, —alk'—COOH, —CH=CH—COOH, —CO—COOH, —C(=NOH)—COOH or —S—alk—COOH radical and/or $R_4$ represents a phenyl radical substituted with a carboxyl radical, with the exception of the compounds containing an alkoxycarbonyl radical, may also be obtained by hydrolysis of a corresponding ester.

This hydrolysis is generally performed by means of a base such as sodium hydroxide or potassium hydroxide, in an inert solvent such as water, tetrahydrofuran, dioxane or a mixture of these solvents, at a temperature in the region of 25° C.

The compounds of formula (I) for which $R_4$ represents a phenyl radical substituted with a hydroxyl radical, with the exception of those containing an alkoxy, alkoxycarbonyl, alkylthio, cycloalkyloxy, cycloalkylalkyloxy, phenylalkyloxy, polyfluoroalkyloxy or cinnamyloxy radical, may also be obtained by hydrolysis of the corresponding compounds for which $R_4$ represents a phenyl radical substituted with an alkoxy radical.

This hydrolysis is preferably performed by means of boron tribromide, in an inert solvent such as a chlorinated solvent (e.g. chloroform, dichloromethane), at a temperature of between −55° C. and 30° C.

The compounds of formula (I) for which $R_3$ represents an optionally substituted phenyl radical or a naphthyl, indolyl or quinolyl radical may be prepared by the action of a derivative of formula (III) on an acid of formula:

$$HOOC-R_3 \qquad (XIX)$$

in which $R_3$ has the same meanings as above, or a reactive derivative of this acid.

This reaction is generally performed under the conditions described above for the reaction of an acid of formula (X) with an amine of formula (XI).

For those skilled in the art, it is understood that, to carry out the processes according to the invention described above, it can be necessary to introduce groups protecting the amino functions in order to avoid side reactions. These functions can, e.g., be blocked in the form of trifluoromethylacetamide and then regenerated by the action of ammoniacal methanol after the process according to the invention has been carried out.

Similarly, when a hydroxyl function is present, it may be necessary to block the said function, e.g. in the form of tert-butyldimethylsilyl or trimethylsilyl ethers, and then to regenerate the function by hydrolysis in an acid medium or by means of fluoride ions after the appropriate process has been carried out.

Similarly, when a carboxyl function is present, it may be necessary to block the said function, e.g. in the form of 4,4-dimethyl-1,3-oxazoline, and then to regenerate the function by hydrolysis in an aqueous or aqueous-alcoholic acid medium after the appropriate process has been carried out, or in the form of a benzyl ester and then to regenerate the function by hydrogenation after the appropriate process has been carried out.

The enantiomers of compounds of formula (I) containing at least one asymmetric center may be obtained by resolution of the racemates, e.g. by chromatography on a chiral column according to W. H. PIRCKLE et al., Asymmetric synthesis, Vol. 1, Academic Press (1983), or by synthesis from chiral precursors.

The compounds of formula (I) may be purified by the usual known methods, e.g. by crystallisation, chromatography, extraction, etc.

The compounds of formula (I) display advantageous pharmacological properties. These compounds possess a strong affinity for cholecystokinin (CCK) receptors and gastrin receptors, and are hence useful in the treatment and prevention of disorders linked to CCK and gastrin at nervous system and gastrointestinal system level.

Thus, these compounds may be used for the treatment or prevention of psychoses, anxiety disorders, Parkinson's disease, tardive dyskinesia, irritable colon syndrome, acute pancreatitis, ulcers, disorders of intestinal motility and certain tumours of the lower oesophagus, colon and intestine, and as an appetite regulator.

These compounds also have a boosting effect on the analgesic activity of narcotic and non-narcotic medicinal products.

The affinity of the compounds of formula (I) for CCK receptors was determined according to a technique based on that of S. SAITO et al., (J. Neuro. Chem., 37, 483–490 (1981)) at cerebral cortical level and at pancreatic level.

In these tests, the $IC_{50}$ of the compounds of formula (1 [sic]) does not generally exceed 1000 nM.

Moreover, it is known that products which recognise central CCK receptors have a similar specificity for the gastrin receptors in the gastrointestinal tract (BOCK et al., J. Med. Chem., 32, 16–23 (1989); REYFELD et al., Am. J. Physiol., 240, G255–266 (1981); BEINFELD et al., Neuropeptides, 3, 411–427 (1983)) .

The compounds of formula (I) are of low toxicity. Administered subcutaneously in mice, their $LD_{50}$ is generally greater than 40 mg/kg.

Of special interest are the compounds of formula (I) for which:

$R_1$ represents a hydrogen atom, $R_2$ represents an alkoxy radical or a radical —$NR_5R_6$, $R_3$ represents a phenylamino radical (in which the phenyl ring is substituted with one or more substituents selected from alkyl, monohydroxyalkyl, carboxyl and —alk—COOH radicals), $R_4$ represents a phenyl radical substituted with one or more substituents selected from halogen atoms, alkoxy, hydroxyl and alkoxycarbonyl radicals and a radical —CO—$NR_5R_6$.

Preferred compounds are the following:

2-{N-(3-methoxyphenyl)-2-[3-(3-methylphenyl)-ureido]acetamido}-N-methyl-N-phenylacetamide 2-{N-(2-chlorophenyl)-2-[3-(3-methylphenyl)-ureido]acetamido}-N-methyl-N-phenylacetamide (RS)-2-[2-{3-[3-(1-hydroxyethyl)phenyl]-ureido} -N-(3-methoxyphenyl)acetamido]-N-methyl-N-phenylacetamide tert-butyl 2-{N-[2-(3,3-dimethylpiperidino)-carbonylphenyl] -2-[3-(3-methylphenyl)ureido]acetamido}-acetate tert-butyl 2-{N-[2-(N-methylanilino)-carbonylphenyl] -2-[3-(3-methylphenyl)ureido]-acetamido} acetate 3-{3-[N-(3-methoxyphenyl)-N-(N-methyl-N-phenylcarbamoylmethyl)carbamoylmethyl] ureido}benzoic acid 3-{3-[N-(3-methoxyphenyl)-N-(N-methyl-N-phenylcarbamoylmethyl)carbamoylmethyl] ureido}-phenylacetic acid 3-{3-[N-(3-hydroxyphenyl)-N-(N-methyl-N-phenylcarbamoylmethyl)carbamoylmethyl] ureido}-phenylacetic acid 3-[3-{N-(3-methoxyphenyl)-N-[2-(1,2,3,4-tetrahydro-1-quinolyl)-2-oxoethyl]carbamoylmethyl}-ureido] benzoic acid tert-butyl 2-{2-[3-(3-methylphenyl)ureido]-N-( 2-tert-butoxycarbonylphenyl)acetamido}acetate (RS)-2-[3-{3-[N-(3-methoxyphenyl)-N-(N -methyl-N-phenylcarbamoylmethyl)carbamoylmethyl]ureido}-phenyl] propionic acid The examples which follow illustrate the invention without limiting it.

EXAMPLE 1

3-Methylphenyl isocyanate (0.6 g) is added at a temperature in the region of 20° C. to a solution of tert-butyl 2-[2-amino-N-(3-chlorophenyl)acetamido]-acetate (1.25 g) in anhydrous tetrahydrofuran (20 cc). The solution obtained is stirred for 4 hours at a temperature in the region of 20° C and then concentrated to dryness under reduced pressure (2.7 kPa) at 40° C. The residual oil is purified by chromatography on silica (0.063–0.2 mm) (150 g) contained in a column 2 cm in diameter [eluent: ethyl cyclohexaneacetane [sic] (75:25 by volume)], collecting 20 cc fractions. The fractions containing only the desired product are combined and concentrated to dryness under reduced pressure (2.7 kPa) at 40° C. After crystallisation in diisopropyl ether, tert-butyl 2-{N-(3-chlorophenyl)-2-[ 3-(3-methylphenyl)ureido]acetamido}acetate (0.8 g), m.p. 110° C. is obtained tert-Butyl 2-[2-amino-N-(3-chlorophenyl)-acetamido] acetate may be prepared in the following manner: hydrazine hydrate (0.75 g) is added to a solution of tert-butyl 2-[N-(3-chlorophenyl)-2-phthalimidoacetamido] acetate (2.4 g) in methanol (40 cc). The reaction mixture is stirred under reflux for 3 hours and then concentrated to dryness under reduced pressure (2.7 kPa) at 40° C. The residue is stirred with diethyl ether (100 cc), the insoluble product is then separated by filtration and the filtrate is concentrated to dryness under reduced pressure (2.7 kPa) at 40° C. tert-Butyl 2-[2-amino-N-(3-chlorophenyl)acetamido] acetate (1.3 g) is thereby obtained in the form of an oil, which is used without further purification in the subsequent syntheses.

tert-Butyl 2-[N-(3-chlorophenyl)-2-phthalimidoacetamido] acetate may be prepared in the following manner: to a solution, maintained under an argon atmosphere, of tert-butyl 2-[(3-chlorophenyl)-amino] acetate (4.8 g) in 1,2-dichforoethane (60 cc), triethylamine (2.8 g) is added, and a solution of 2-phthalimidoacetyl chloride (6.2 g) in 1,2-dichloroethane (20 cc) is then added dropwise at a temperature in the region of 20° C. The solution obtained is stirred for 3 hours at a temperature in the region of 20° C. and then treated with water (50 cc). The aqueous phase is separated after settling has taken place and then re-extracted with 1,2-dichloroethane (2×50 cc). The organic phases are combined, washed with water (2×10 cc), dried over magnesium sulphate, filtered and then concentrated to dryness under reduced pressure (2.7 kPa) at 40° C. The oil obtained is purified by chromatography on silica (0,063–0.2 mm) (200 g) contained in a column 2.5 cm in diameter [eluent: cyclohexane/ethyl acetate (50:50 by volume)], collecting 25-cc fractions. Fractions 3 to 7 are combined and concentrated to dryness under reduced pressure (2.7 kPa) at 40° C. tert-Butyl 2-[N-(3-chlorophenyl)- 2-phthalimidoacetamido] acetate (2.6 g) is thereby obtained in the form of an oil, which is used without further purification in the subsequent syntheses.

tert-Butyl 2-[(3-chlorophenyl)amino]acetate may be prepared in the following manner: tert-butyl bromoacetate (5.9 g) is added to a solution of 3-chloroaniline (7.6 g) in acetonitrile (60 cc). The solution obtained is stirred under reflux for 4 hours. After cooling, the insoluble product is separated by filtration and washed with acetonitrile (30 cc). The filtrates are combined and concentrated to dryness under reduced pressure (2.7 kPa) at 40° C. The residual oil is dissolved in dichloromethane (150 cc) and the solution obtained is washed with water (4×15 cc). The organic phase is dried over magnesium sulphate, filtered and then concentrated to dryness under reduced pressure (2.7 kPa) at 40° C. tert-Butyl 2-[(3-chlorophenyl)amino] acetate (8.1 g) is thereby obtained in the form of an oil, which is used without further purification in the subsequent syntheses.

2-Phthalimidoacetyl chloride may be prepared according to the method described by W. GRASSMANN and E. SCHULTE-UEBBING, Chem. Ber., 83, 244–247, (1950).

EXAMPLE 2

Using a procedure similar to that described in Example 1, but starting with tert-butyl 2-[2-amino-N-( 2-fluorophenyl)acetamido]acetate (2.5 g) and 3-methylphenyl isocyanate (1.2 g), and after recrystallisation in diisopropyl ether, tert-butyl 2-{N-(2-fluorophenyl)-2-[3-(3-methylphenyl)ureido]-acetamido} acetate (1.75 g), m.p. 148° C., is obtained.

tert-Butyl 2-[2-amino-N-(2-fluorophenyl)-acetamido] acetate may be prepared in a manner similar to that described in Example 1 for the preparation of tert-butyl 2-[2-amino-N-(3-chlorophenyl)acetamido]-acetate, but starting with tert-butyl 2-[N-(2-fluorophenyl)- 2-phthalimidoacetamido]acetate (4.9 g) and hydrazine hydrate (0.77 g). tert-Butyl 2-[2-amino-N-(2-fluorophenyl)acetamido] acetate (2.7 g) is thereby obtained in the form of an oil, which is used without further purification in the subsequent syntheses.

tert-Butyl 2-[N-(2-fluorophenyl)- 2-phthalimidoacetamido]acetate may be prepared in the following manner: to a solution, maintained under an argon atmosphere, of tert-butyl 2-[(2-fluorophenyl)-amino] acetate (3.3 g) in 1,2-dichloroethane (60 cc), sodium hydrogen carbonate (1.3 g) is added, and a solution of 2-phthalimidoacetyl chloride (3.1 g) in 1,2-dichloroethane (10 cc) is then added dropwise at a temperature in the region of 20° C. The solution obtained is stirred for 3 hours at a temperature in the region of 20° C. and then treated with water (20 cc). The aqueous phase is separated off after settling has taken place and then re-extracted with 1,2-dichloroethane (2×100 cc). The organic phases are combined, dried over magnesium sulphate, filtered and then concentrated to dryness under reduced pressure (2.7 kPa) at 40° C. After recrystallisation in petroleum ether, tert-butyl 2-[N-(2-fluorophenyl)-2-phthalimidoacetamido]acetate (4.9 g), m.p. 140° C., is obtained.

tert-Butyl 2-[(2-fluorophenyl)amino]acetate may be prepared in a manner similar to that described in Example 1 for the preparation of tert-butyl 2-[(3-chlorophenyl)amino] acetate, but starting with 2-fluoro-aniline (2.45 g) and tert-butyl bromoacetate (1.95 g). After recrystallisation in petroleum ether, tert-butyl 2-[(2-fluorophenyl)amino]acetate (1.1 g), m.p. 70° C., is thereby obtained.

EXAMPLE 3

Using a procedure similar to that described in Example 1, but starting with tert-butyl 2-[2-amino-N-(4-methoxyphenyl)acetamido]acetate (6.6 g) and 3-methylphenyl isocyanate (3 g), and after recrystallisation in acetonitrile, tert-butyl 2-{N-(4-methoxyphenyl)- 2-[3-(3-methylphenyl)ureido]acetamido}-acetate (1.7 g), m.p. 158° C., is obtained.

tert-Butyl 2-[2-amino-N-(4-methoxyphenyl)-acetamido]acetate may be prepared in a manner similar to that described in Example 1 for the preparation of tert-butyl 2-[2-amino-N-(3-chlorophenyl)acetamido]-acetate, but starting with tert-butyl 2-[N-(4-methoxyphenyl)- 2-phthalimidoacetamido]acetate (11.7 g) and hydrazine hydrate (1.75 g). tert-Butyl 2-[2-amino-N-(4-methoxyphenyl)acetamido]acetate (7 g) is thereby obtained in the form of an oil, which is used without further purification in the subsequent syntheses.

tert-Butyl 2-[N-(4-methoxyphenyl)-2-phthalimidoacetamido] acetate may be prepared in a manner similar to that described in Example 2 for the preparation of tert-butyl 2-[2-phthalimido-N-(2-fluorophenyl)acetamido] acetate, but starting with tert-butyl 2-[(4-methoxyphenyl)amino]acetate (6.7 g), sodium hydrogen carbonate (2.5 g) and 2-phthalimidoacetyl chloride (6.25 g). tert-Butyl 2-[2-phthalimido-N-(4-methoxyphenyl)acetamido] acetate (11.7 g) is thereby obtained in the form of an oil, which is used without further purification in the subsequent syntheses.

tert-Butyl 2-[(4-methoxyphenyl)amino]acetate may be prepared in a manner similar to that described in Example 1 for the preparation of tert-butyl 2-[(3-chlorophenyl)amino]acetate, but starting with 4-methoxyaniline (7.3 g) and tert-butyl bromoacetate (5.95 g). tert-Butyl 2-[(4-methoxyphenyl)amino]acetate (7.2 g) is thereby obtained in the form of an oil, which is used without further purification in the subsequent syntheses.

EXAMPLE 4

Using a procedure similar to that described in Example 1, but starting with tert-butyl 2-[2-amino-N-( 2-trifluoromethoxyphenyl)acetamino]acetate (2 g) and 3-methylphenyl isocyanate (0.8 g), and after recrystallisation in ethyl acetate, tert-butyl 2-{2-[3-(3-methylphenyl)ureido]-N-(2-trifluoromethoxyphenyl)acetamido} acetate (1.35 g), m.p. 163° C., is obtained.

tert-Butyl 2-[2-amino-N-(2-trifluoromethoxyphenyl)acetamido] acetate may be prepared in the following manner: hydrazine hydrate (1.5 g) is added to a solution of tert-butyl 2-[2-phthalimido-N-(2-trifluoromethoxyphenyl)acetamido] acetate (4.4 g) in ethanol (50 cc). The reaction mixture is stirred for 3 hours at a temperature in the region of 20° C. and then concentrated to dryness under reduced pressure (2.7 kPa) at 40° C. The residue is stirred with diethyl ether (200 cc) and the insoluble product is separated by filtration. The filtrate is concentrated to dryness under reduced pressure (2.7 kPa) at 40° C. tert-Butyl 2-[2-amino-N-(2-trifluoromethoxyphenyl)acetamido]-acetate (2.1 g) is thereby obtained in the form of an oil, which is used without further purification in the subsequent syntheses.

tert-Butyl 2-[2-phthalimido-N-(2-trifluoromethoxyphenyl)acetamido] acetate may be prepared in the following manner: an oily suspension (50% by weight) (0.7 g) of sodium hydride is added at a temperature in the region of 10° C. to a solution, maintained under an argon atmosphere, of 2-phthalimido-N-(2-trifluoromethoxyphenyl)acetamide (5 g) in anhydrous tetrahydrofuran (50 cc), and the suspension obtained is stirred for 1 hour at a temperature in the region of 20° C. A solution of tert-butyl bromoacetate (2.75 g) in anhydrous tetrahydrofuran (10 cc) is then added and stirring is continued for 3 hours at a temperature in the region of 20° C. The reaction mixture is then poured into a mixture, cooled to a temperature in the region of 0° C., of water (20 cc) and ethyl acetate (200 cc). The aqueous phase is separated after settling has taken place and re-extracted with ethyl acetate (2×20 cc). The organic phases are combined, washed with water (3×25 cc), dried over magnesium sulphate, filtered and then concentrated to dryness under reduced pressure (2.7 kPa) at 40° C. tert-Butyl 2-[2-phthalimido-N-(2-trifluoromethoxyphenyl)acetamido] acetate (4.4 g) is thereby obtained in the form of an oil, which is used without further purification in the subsequent syntheses.

2-Phthalimido-N-(2-trifluoromethoxyphenyl)-acetamide may be prepared in the following manner: to a solution, maintained under an argon atmosphere, of 2-trifluoromethoxyaniline (3.6 g) in dichloromethane (50 cc), triethylamine (2.2 g) is added, and a solution of 2-phthalimidoacetyl chloride (4.6 g) in dichloromethane (25 cc) is then added while the temperature is maintained in the region of 20° C. The solution obtained is stirred for 3 hours at a temperature in the region of 20° C. and then treated with water (25 cc). The solid formed is separated by filtration, washed with dichloromethane (3×5 cc) and then with water (3×10 cc) and dried in the air. The organic phase of the filtrate is separated after settling has taken place, washed with distilled water (2×10 cc), dried over magnesium sulphate, filtered and then concentrated to dryness under reduced pressure (2.7 kPa) at 40° C. The solid obtained is combined with the above solid and the whole is recrystalised in ethyl acetate. 2-Phthalimido-N-(2-trifluoromethoxyphenyl)acetamide (5.1 g), m.p. 192° C., is thereby obtained.

EXAMPLE 5

Using a procedure similar to that described in Example 1, but starting with tert-butyl 2-[2-amino-N-( 3-trifluoromethoxyphenyl)acetamido]acetate (3.4 g) and 3-methylphenyl isocyanate (1.4 g), and after recrystallisation in diisopropyl ether, tert-butyl 2-{2-[3-(3-methylphenyl)ureido]-N-(3-trifluoromethoxyphenyl)acetamido} acetate (1.75 g), m.p. 125° C., is obtained.

tert-Butyl 2-[2-amino-N-(3-trifluoromethoxyphenyl)acetamido] acetate may be prepared in a manner similar to that described in Example 4 for the preparation of tert-butyl 2-[2-amino-N-(2-trifluoromethoxyphenyl)acetamido] acetate, but starting with tert-butyl 2-[2-phthalimido-N-(3-trifluoromethoxyphenyl)acetamido] acetate (3 g) and hydrazine hydrate (3.2 g). tert-Butyl 2-[2-amino-N-(3-trifluoromethoxyphenyl)acetamido] acetate (3.5 g) is thereby obtained in the form of an oil, which is used without further purification in the subsequent syntheses.

tert-Butyl 2-[2-phthalimido-N-(3-trifluoromethoxyphenyl)acetamido] acetate may be prepared in a manner similar to that described in Example 4 for the preparation of tert-butyl 2-[2-phthalimido-N-(2-trifluoromethoxyphenyl)acetamido] acetate, but starting with 2-phthalimido-N-(3-trifluoromethoxyphenyl)acetamide (4.8 g), an oily suspension (50% by weight) (0.7 g) of sodium hydride and tert-butyl bromoacetate (2.75 g). tert-Butyl 2-[2-phthalimido-N-( 3-trifluoromethoxy-phenyl)acetamido] acetate (5.1 g) is thereby obtained in the form of an oil, which is used without further purification in the subsequent syntheses.

2-Phthalimido-N-(3-trifluoromethoxyphenyl)acetamide may be prepared in a manner similar to that described in Example 4 for the preparation of 2-phthalimido-N-(2-trifluoromethoxyphenyl)acetamide, but starting with 3-trifluoromethoxyaniline (3.6 g), triethylamine (2.2 g) and 2-phthalimidoacetyl chloride (4.6 [lacuna]). After recrystallisation in ethyl acetate, 2-phthalimido-N-(3-trifluoromethoxyphenyl)acetamide (4.8 g), m.p. 170° C., is thereby obtained.

EXAMPLE 6

Using a procedure similar to that described in Example 1, but starting with tert-butyl 2-[2-amino-N-(3-methylphenyl)acetamido]acetate (3.1 g) and 3-methylphenyl isocyanate (0.52 g), and after recrystallisation in diisopropyl ether, tert-butyl 2-{2-[3-(3-methylphenyl)ureido]-N-3-methylphenyl)acetamido} acetate (1.2 g), m.p. 97° C. is obtained.

tert-Butyl 2-[2-amino-N-(3-methylphenyl)acetamido] acetate may be prepared in a manner similar to that described in Example 4 for the preparation of tert-butyl 2-[2-amino-N-(2-trifluoromethoxyphenyl)acetamido] acetate, but starting with tert-butyl 2-[N-(3-methylphenyl)-2-phthalimidoacetamido]acetate (7.5 g) and hydrazine hydrate (1.84 g). tert-Butyl 2-[2-amino-N-(3-methylphenyl)acetamido]acetate (3.5 g) is thereby obtained in the form of an oil, which is used without further purification in the subsequent syntheses.

tert-Butyl 2-[N-(3-methylphenyl)-2-phthalimidoacetamido] acetate may be prepared in a manner similar to that described in Example 4 for the preparation of tert-butyl 2-[2-phthalimido-N-(2-trifluoromethoxyphenyl)acetamido] acetate, but starting with N-(3-methylphenyl)-2-phthalimidoacetamide (12.5 g), an oily suspension (50% by weight) (2.45 g) of sodium hydride and tert-butyl bromoacetate (8.3 g). After recrystallisation in diisopropyl ether, tert-butyl 2-[N-(3-methylphenyl)-2-phthalimidoacetamido] acetate (7.6 g), m.p. 166° C., is thereby obtained.

N-(3-Methylphenyl)-2-phthalimidoacetamide may be prepared in a manner similar to that described in Example 4 for the preparation of 2-phthalimido-N-(2-trifluoromethoxyphenyl)acetamide, but starting with 3-methylaniline (5.36 g), triethylamine (5.1 g) and 2-phthalimidoacetyl chloride (11.2 g). N-(3-Methyl-phenyl)-2-phthalimidoacetamide (12.7 g), m.p. 207° C., is thereby obtained.

EXAMPLE 7

Using a procedure similar to that described in Example 1, but starting with 2-[2-amino-N-(3-methoxyphenyl)acetamido] -N-methyl-N-phenylacetamide (1.6 g) and 3-methylphenyl isocyanate (0.67 g), and after recrystallisation in acetonitrile, 2-{N-(3-methoxyphenyl)- 2-[3-(3-methylphenyl)ureido]acetamido}-N-methyl-N-phenylacetamide (1.2 g), m.p. 179° C., is obtained.

2-[2-Amino-N-(3-methoxyphenyl)acetamido] -N-methyl-N-phenylacetamide may be prepared in a manner similar to that described in Example 4 for the preparation of tert-butyl 2-[2-amino-N-(2-trifluoromethoxyphenyl)acetamido] acetate, but starting with 2-[N-(3-methoxyphenyl)-2-phthalimidoacetamido] -N-methyl-N-phenylacetamide (2.3 g) and hydrazine hydrate (0.75 g). 2-[2-Amino-N-(3-methoxyphenyl)acetamido] -N-methyl-N-phenylacetamide (1.6 g) is thereby obtained in the form of an oil, which is used without further purification in the subsequent syntheses.

2-[N-(3-Methoxyphenyl)-2-phthalimidoacetamido] -N-methyl-N-phenylacetamide may be prepared in a manner similar to that described in Example 4 for the preparation of tert-butyl 2-[2-phthalimido-N-( 2-trifluoromethoxyphenyl)acetamido]acetate, but starting with N-(3-methoxyphenyl)-2-phthalimidoacetamide (9.15 g), an oily suspension (50% by weight) (1.6 g) of sodium hydride and 2-bromo-N-methyl-N-phenylacetamide (7.4 g). 2-[N-(3-Methoxyphenyl)-2-phthalimidoacetamido] -N-methyl-N-phenylacetamide (5.7 g) is thereby obtained in the form of a resin, which is used without further purification in the subsequent syntheses.

N-(3-Methoxyphenyl)-2-phthalimidoacetamide may be prepared in a manner similar to that described in Example 4 for the preparation of 2-phthalimido-N-( 2-trifluoromethoxyphenyl)acetamide, but starting with 3-methoxyaniline (6.15 g), triethylamine (5.6 g) and 2-phthalimidoacetyl chloride (11.2 g). After recrystallisation in acetonitrile, 2-phthalimido-N-( 3-methoxyphenyl)acetamide (12.3 g), m.p. 186° C., is thereby obtained.

EXAMPLE 8

Using a procedure similar to that described in Example 1, but starting with tert-butyl 2-[2-amino-N-( 3-trifluoromethylphenyl)acetamido]acetate (4.9 g) and 3-methylphenyl isocyanate (2 g), and after recrystallisation in diisopropyl ether, tert-butyl 2-{2-[3-(3-methylphenyl)ureido]-N-(3-trifluoromethylphenyl)acetamido} acetate (1.56 g), m.p. 140° C., is obtained.

tert-Butyl 2-[2-amino-N-(3-trifluoromethylphenyl)acetamido] acetate may be prepared in a manner similar to that described in Example 4 for the preparation of tert-butyl 2-[2-amino-N-(2-trifluoromethoxyphenyl)acetamido] acetate, but starting with tert-butyl 2-[2-phthalimido-N-(3-trifluoromethylphenyl)acetamido] acetate (9 g) and hydrazine hydrate (2.9 g). tert-Butyl 2-[2-amino-N-(3-trifluoromethylphenyl)acetamido] acetate (5.2 g) is thereby obtained in the form of an oil, which is used without further purification in the subsequent syntheses.

tert-Butyl 2-[2-phthalimido-N-(3-trifluoromethylphenyl)acetamido] acetate may be prepared in a manner similar to that described in Example 4 for the preparation of tert-butyl 2-[2-phthalimido-N-(2-trifluoromethoxyphenyl)acetamido] acetate, but starting with 2-phthalimido-N-(3-trifluoromethylphenyl)acetamide (16.5 g), an oily suspension (50% by weight) (2.3 g) of sodium hydride and tert-butyl bromoacetate (9.2 g). tert-Butyl 2-[2-phthalimido-N-(3-trifluoromethylphenyl)acetamido] acetate (9.1 g) is thereby obtained in the form of an oil, which is used without further purification in the subsequent syntheses.

2-Phthalimido-N-(3-trifluoromethylphenyl)-acetamide may be prepared in a manner similar to that described in Example 4 for the preparation of 2-phthalimido-N-(2-trifluoromethoxyphenyl)acetamide, but starting with 3-trifluoromethylaniline (8.1 g), triethylamine (5.1 g) and 2-phthalimidoacetyl chloride (11.2 g). 2-Phthalimido-N-(3-trifluoromethylphenyl)acetamide (16.7 g), m.p. 235° C., is thereby obtained.

EXAMPLE 9

Using a procedure similar to that described in Example 1, but starting with tert-butyl 2-[2-amino-N-( 2-ethoxycarbonylphenyl)acetamido]acetate (3.6 g) and 3-methylphenyl isocyanate (1.42 g), and after recrystallisation in diisopropyl ether, tert-butyl 2-{N-(2-ethoxycarbonylphenyl)-2-[3-(3- methylphenyl)ureido] acetamido}acetate (1.35 g), m.p. 142° C., is obtained.

tert-Butyl 2-[2-amino-N-(2-ethoxycarbonylphenyl)acetamido] acetate may be prepared in a manner similar to that described in Example 4 for the preparation of tert-butyl 2-[2-amino-N-(2-trifluoromethoxyphenyl)acetamido] acetate, but starting with tert-butyl 2-[N-(2-ethoxycarbonylphenyl)-2-phthalimidoacetamido] acetate (6.13 g) and hydrazine hydrate (1.98 g). tert-Butyl 2-[2-amino-N-(2-ethoxycarbonylphenyl)acetamido] acetate (3.6 g) is thereby obtained in the form of an oil, which is used without further purification in the subsequent syntheses.

tert-Butyl 2-[N-(2-ethoxycarbonylphenyl)-2-phthalimidoacetamido] acetate may be prepared in a manner similar to that described in Example 4 for the preparation of tert-butyl 2-[2-phthalimido-N-(2-trifluoromethoxyphenyl)acetamido] acetate, but starting with N-(2-ethoxycarbonylphenyl)-2-phthalimidoacetamide (7.7 g), an oily suspension (50% by weight) (1.26 g) of sodium hydride and tert-butyl bromoacetate (4.3 g). After recrystallisation in diisopropyl ether, tert-butyl 2-[N-(2-ethoxycarbonylphenyl)-2-phthalimidoacetamido] acetate (6.1 g), m.p. 127° C., is thereby obtained.

N-(2-Ethoxycarbonylphenyl)-2-phthalimidoacetamide may be prepared in a manner similar to that described in Example 4 for the preparation of 2-phthalimido-N-(2-trifluoromethoxyphenyl)acetamide, but starting with ethyl 2-aminobenzoate (4.13 g), triethylamine (2.8 g) and 2-phthalimidoacetyl chloride (5.6 g). N-(2-Ethoxycarbonylphenyl)-2-phthalimidoacetamide (7.7 g), m.p. 187° C., is thereby obtained.

EXAMPLE 10

Using a procedure similar to that described in Example 1, but starting with tert-butyl 2-{2-amino-N-[ 2-(acetylamino)phenyl]acetamido}acetate (4.7 g) and 3-methylphenyl isocyanate (2 g), and after recrystallisation in ethyl acetate, tert-butyl 2-{N-[2-(acetylamino)phenyl] -2-[3-(3-methylphenyl)ureido]acetamido} acetate (3.6 g), m.p. 185° C., is obtained.

tert-Butyl 2-{2-amino-N-[2-(acetylamino)-phenyl] acetamido}acetate may be prepared in a manner similar to that described in Example 4 for the preparation of tert-butyl 2-[2-amino-N-(2-trifluoromethoxyphenyl)acetamido] acetate, but starting with tert-butyl 2-{N-[2-(acetylamino)phenyl]-2-phthalimidoacetamido} acetate (7.2 g) and hydrazine hydrate (2.4 g). tert-Butyl 2-{2-amino-N-[2-(acetylamino)phenyl] acetamido}acetate (4.8 g) is thereby obtained in the form of an oil, which is used without further purification in the subsequent syntheses.

tert-Butyl 2-{N-[2-(acetylamino)phenyl]-2-phthalimidoacetamido} acetate may be prepared in a manner similar to that described in Example 4 for the preparation of tert-butyl 2-[2-phthalimido-N-(2-trifluoromethoxyphenyl)acetamido] acetate, but starting with N-[2-(acetylamino)phenyl]-2-phthalimidoacetamide (9.7 g), an oily suspension (50% by weight) (1.6 g) of sodium hydride and tert-butyl bromoacetate (5.85 g). After recrystallisation in ethyl acetate, tert-butyl 2-{N-[2-(acetylamino)phenyl]-2-phthalimidoacetamido}acetate (8 g), m.p. 170° C., is thereby obtained.

N-[2-(Acetylamino)phenyl]-2-phthalimidoacetamide may be prepared in a manner similar to that described in Example 4 for the preparation of 2-phthalimido-N-(2-trifluoromethoxyphenyl)acetamide, but starting with 2-(acetylamino)aniline (6 g), triethylamine (4.05 g) and 2-phthalimidoacetyl chloride (9.6 g). N-[2-(Acetylamino)phenyl]-2-phthalimidoacetamide (12.5 g), m.p. 270° C., is thereby obtained.

EXAMPLE 11

Using a procedure similar to that described in Example 1, but starting with tert-butyl 2-[2-amino-N-( 2-chlorophenyl)acetamido]acetate (4.8 g) and 3-methylphenyl isocyanate (2.35 g), and after recrystallisation in a mixture of ethyl acetate and methanol (80:20 by volume), tert-butyl 2-{N-(2-chlorophenyl)- 2-[3-(3-methylphenyl)ureido] acetamido}acetate (1.4 g), m.p. 148° C., is obtained.

tert-Butyl 2-[2-amino-N-(2-chlorophenyl)acetamido] acetate may be prepared in a manner similar to that described in Example 1 for the preparation of tert-butyl 2-[2-amino-N-(3-chlorophenyl)acetamido]acetate, but starting with tert-butyl 2-[N-(2-chlorophenyl)- 2-phthalimidoacetamido]acetate (9.12 g) and hydrazine hydrate (1 g). tert-Butyl 2-[2-amino-N( 2-chlorophenyl)acetamido]acetate (5.2 g) is thereby obtained in the form of an oil, which is used without further purification in the subsequent syntheses.

tert-Butyl 2-[N-(2-chlorophenyl)-2-phthalimidoacetamido] acetate may be prepared in a manner similar to that described in Example 2 for the preparation of tert-butyl 2-[N-(2-fluorophenyl)-2-phthalimidoacetamido] acetate, but starting with tert-butyl 2-[(2-chlorophenyl)amino]acetate (8 g), sodium hydrogen carbonate (3.1 g) and 2-phthalimidoacetyl chloride (7.4 g). After recrystallisation in a mixture of ethyl acetate and cyclohexane (70:30 by volume), tert-butyl 2-[N-(2-chlorophenyl)-2-phthalimidoacetamido] acetate (10.6 g), m.p. 164° C., is obtained.

tert-Butyl 2-[(2-chlorophenyl)amino]acetate may be prepared in a manner similar to that described in Example 1 for the preparation of tert-butyl 2-[(3-chlorophenyl)amino]acetate, but starting with 2-chloroaniline (19.1 g) and tert-butyl bromoacetate (9.75 g). tert-Butyl 2-[(2-chlorophenyl)amino]acetate (9.3 g) is thereby obtained in the form of an oil, which is used without further purification in the subsequent syntheses.

EXAMPLE 12

Using a procedure similar to that described in Example 1, but starting with tert-butyl 2-[2-amino-N-( 3,4-methylenedioxyphenyl)acetamido]acetate (2.4 g) and 3-methylphenyl isocyanate (1 g), and after recrystallisation in ethyl acetate, tert-butyl 2-{N-(3,4-methylenedioxyphenyl)-2-[3-(3-methylphenyl)ureido] acetamido}acetate (1.65 g), m.p. 142° C., is obtained.

tert-Butyl 2-[2-amino-N-(3,4-methylenedioxyphenyl)acetamido] acetate may be prepared in the following manner: methyl hydrazine (1.45 g) is added at a temperature in the region of 0° C. to a solution of tert-butyl 2-[N-(3,4-methylenedioxyphenyl)-2-phthalimidoacetamido] acetate (4.6 g) in dichloromethane (70 cc). The reaction mixture is stirred for 16 hours at a temperature in the region of 20° C. and then for 2 hours under reflux of the dichloromethane, and cooled to a temperature in the region of 20° C. Water (50 cc) is added, the mixture is stirred and the aqueous phase is separated off after settling has taken place and re-extracted with dichloromethane (2×40 cc). The organic phases are combined, dried over magnesium sulphate, filtered and then concentrated to dryness under reduced pressure (2.7 kPa) at 40° C. The oil obtained is purified by chromatography on silica (0.063–0.2 mm) (50 g) contained in a column 2 cm in diameter [eluent: ethyl acetate/methanol (90:10 by volume)], collecting 20-cc fractions. Fractions 11 to 22 are combined and concentrated to dryness under reduced pressure (2.7 kPa) at 40° C. tert-Butyl 2-[2-amino-N-(3,4-methylenedioxyphenyl)acetamido] acetate (1.85 g) is thereby obtained in the form of an oil, which is used without further purification in the subsequent synthesis.

tert-Butyl 2-[N-(3,4-methylenedioxyphenyl)-2-phthalimidoacetamido] acetate may be prepared in a manner similar to that described in Example 2 for the preparation of tert-butyl 2-[N-(2-fluorophenyl)-2-phthalimidoacetamido] acetate, but starting with tert-butyl 2-[(3,4-methylenedioxyphenyl)amino]acetate (5.15 g), sodium hydrogen carbonate (1.9 g) and 2-phthalimidoacetyl chloride (4.6 g). After recrystallisation in ethyl acetate, tert-butyl 2-[N-(3,4-methylenedioxyphenyl)-2-phthalimidoacetamido] acetate (8 g), m.p. 166° C., is obtained.

tert-Butyl 2-[(3,4-methylenedioxyphenyl)amino] acetate may be prepared in a manner similar to that described in Example 1 for the preparation of tert-butyl 2-[(3-chlorophenyl)amino]acetate, but starting with 3,4-methylenedioxyaniline (9 g) and tert-butyl bromoacetate (5.9 g). After recrystallisation in petroleum ether, tert-butyl 2-[(3,4-methylenedioxyphenyl)amino] acetate (5.2 g), m.p. 80° C., is thereby obtained.

EXAMPLE 13

3-Methylphenyl isocyanate (0.35 g) is added at a temperature in the region of 20° C. to a solution of tert-butyl 2-[2-amino-N-(4-dimethylaminophenyl)acetamido] acetate (0.7 g) in anhydrous tetrahydrofuran (15 cc). The solution obtained is stirred for 3 hours at a temperature in the region of 20° C. and then concentrated to dryness under reduced pressure (2.7 kPa) at 40° C. After recrystallisation of the residual solid in ethyl acetate, tert-butyl 2-{N-(4-dimethylaminophenyl)-2-[3-(3-methylphenyl)ureido] acetamido}acetate (0 7 g), m.p 105° C., is obtained.

tert-Butyl 2-[2-amino-N-(4-dimethylaminophenyl)acetamido] acetate may be prepared in the following manner: hydrazine hydrate (0.15 g) is added to a solution of tert-butyl 2-[N-(4-dimethylaminophenyl)- 2-phthalimidoacetamido] acetate (1 g) in methanol (20 cc). The reaction mixture is stirred under reflux for 3 hours and then concentrated to dryness under reduced pressure (2.7 kPa) at 40° C. The residue is stirred with diethyl ether (75 cc) and the insoluble product is separated by filtration. The filtrate is concentrated to dryness under reduced pressure (2.7 kPa) at 40° C. tert-Butyl 2-[2-amino-N-(4-dimethylaminophenyl)acetamido] acetate (0.7 g) is thereby obtained in the form of an oil, which is used without further purification in the subsequent syntheses.

tert-Butyl 2-[N-(4-dimethylaminophenyl)-2-phthalimidoacetamido] acetate may be prepared in the following manner: to a solution, maintained under an argon atmosphere, of tert-butyl 2-[(4-dimethylaminophenyl)amino] acetate (2.6 g) in 1,2-dichloroethane (20 cc), triethylamine (1.4 g) is added, and a solution of 2-phthalimidoacetyl chloride (3.1 g) in 1,2-dichloroethane (20 cc) is then added dropwise at a temperature in the region of 20° C. The solution obtained is stirred for 3 hours at a temperature in the region of 20° C. and then treated with water (25 cc). The aqueous phase is separated after settling has taken place and then re-extracted with 1,2-dichloroethane (2×50 cc). The organic phases are combined, washed with water (2×10 cc), dried over magnesium sulphate, filtered and then concentrated to dryness under reduced pressure (2.7 kPa) at 40° C. The oil obtained is purified by chromatography on silica (0.063–0.2 mm) (100 g) contained in a column 2 cm in diameter [eluent: dichloromethane/methanol (98:2 by volume)], collecting 15-cc fractions. The fractions containing only the desired product are combined and concentrated to dryness under reduced pressure (2.7 kPa) at 40° C. tert-Butyl 2-[N-(4-dimethylaminophenyl)-2-phthalimidoacetamido] acetate (1.1 g), m.p. 170° C., is thereby obtained.

tert-Butyl 2-[(4-dimethylaminophenyl)amino]acetate may be prepared in the following manner: triethylamine (6.1 g) is added at a temperature in the region of 10° C. to a suspension of 4-dimethylaminoaniline dihydrochloride (6.3 g) in acetonitrile (50 cc). The suspension obtained is stirred for 30 minutes at a temperature in the region of 20° C., tert-butyl bromoacetate (3 g) is then added and the reaction mixture is stirred under reflux for 4 hours. After cooling, the insoluble product is separated by filtration and washed with acetonitrile (15 cc). The filtrates are combined and concentrated to dryness under reduced pressure (2.7 kPa) at 40° C. The residual oil is dissolved in dichloromethane (100 cc) and the solution obtained is washed with water (4×10 cc). The organic phase is dried over magnesium sulphate, filtered and then concentrated to dryness under reduced pressure (2.7 kPa) at 40° C. tert-Butyl 2-[(4-dimethylaminophenyl)amino] acetate (2.6 g) is thereby obtained in the form of an oil, which is used without further purification in the subsequent syntheses.

EXAMPLE 14

Using a procedure similar to that described in Example 11, but starting with tert-butyl 2-[2-amino-N-( 3-methylthiophenyl)acetamido]acetate (5.1 g) and 3-methylphenyl isocyanate (2.2 g), and after recrystallisation in a mixture of diisopropyl ether and ethyl acetate (80:20 by volume), tert-butyl 2-{2-[3-(3methylphenyl)ureido] -N-(3-methylthiophenyl)acetamido] acetate (2.6 g), m.p. 135° C., is obtained.

tert-Butyl 2-[2-amino-N-(3-methylthiophenyl)acetamido] acetate may be prepared in a manner similar to that described in Example 1 for the preparation of tert-butyl 2-[2-amino-N-(3-chlorophenyl)acetamido]acetate, but starting with tert-butyl 2-[N-(3-methylthiophenyl)- 2-phthalimidoacetamido]acetate (7.6 g) and hydrazine hydrate (2.6 g) and working at a temperature in the region of 20° C. tert-Butyl 2-[2-amino-N-(3-methylthiophenyl)acetamido] acetate (5.1 g) is thereby obtained in the form of an oil, which is used without further purification in the subsequent syntheses.

tert-Butyl 2-[N-(3-methylthiophenyl)-2-phthalimidoacetamido] acetate may be prepared in a manner similar to that described in Example 1 for the preparation of tert-butyl 2-[N-(3-chlorophenyl)-2-phthalimidoacetamido] acetate, but starting with tert-butyl 2-[(3-methylthiophenyl)amino] acetate (6.8 g), triethylamine (3 g) and 2-phthalimidoacetyl chloride (6 g). After crystallisation in diisopropyl ether, tert-butyl 2-[N-(3-methylthiophenyl)-2-phthalimidoacetamido] acetate (7.6 g), m.p. 141° C., is thereby obtained.

tert-Butyl 2-[(3-methylthiophenyl)amino]acetate may be prepared in a manner similar to that described in Example 1 for the preparation of tert-butyl 2-[(3-chlorophenyl)amino] acetate, but starting with 3-methylthioaniline (8.4 g) and tert-butyl bromoacetate (5.9 g). tert-Butyl 2-[(3-methylthiophenyl)amino] acetate (6.8 g) is thereby obtained in the form of an oil, which is used without further purification in the subsequent syntheses.

EXAMPLE 15

Using a procedure similar to that described in Example 11, but starting with 2-[2-amino-N-(2-chlorophenyl)acetamido] -N-methyl-N-phenylacetamide (3.4 g) and 3-methylphenyl isocyanate (1.4 g), and after recrystallisation in acetonitrile, 2-{N-(2-chlorophenyl)- 2-[3-(3-methylphenyl)ureido]acetamido}-N-methyl-N-phenylacetamide (2.2 g), m.p. 180° C., is obtained.

2-[2-Amino-N-(2-chlorophenyl)acetamido] -N-methyl-N-phenylacetamide may be prepared in a manner similar to that described in Example 4 for the preparation of tert-butyl 2-[2-amino-N-(2-trifluoromethoxyphenyl)acetamido] acetate, but starting with 2-[N-(2-chlorophenyl)-2-phthalimidoacetamido] -N-methyl-N-phenylacetamide (5.6 g) and hydrazine hydrate (1.9 g). 2-[2-Amino-N-(2-chlorophenyl)acetamido] -N-methyl-N-phenylacetamide (3.3 g) is thereby obtained in the form of an oil, which is used without further purification in the subsequent syntheses.

2-[N-(2-Chlorophenyl)-2-phthalimidoacetamido] -N-methyl-N-phenylacetamide may be prepared in a manner similar to that described in Example 4 for the preparation of tert-butyl 2-[2-phthalimido-N-( 2-trifluoromethoxyphenyl)acetamido]acetate, but starting with 2-phthalimido-N-(2-chlorophenyl)acetamide (7.4 g), an oily suspension (50% by weight) (1.3 g) of sodium hydride and 2-bromo-N-methyl-N-phenylacetamide (5.9 g). After recrystallisation in ethyl acetate, 2-[N-(2-chlorophenyl)-2-phthalimidoacetamido] -N-methyl-N-phenylacetamide (5.7 g), m.p. 168° C., is thereby obtained.

2-Phthalimido-N-(2-chlorophenyl)acetamide may be prepared in a manner similar to that described in Example 4 for the preparation of 2-phthalimido-N-( 2-trifluoromethoxyphenyl)acetamide, but starting with 2-chloroaniline (3.8 g), triethylamine (3.3 g) and 2-phthalimidoacetyl chloride (7.2 g). N-(2-Chlorophenyl)- 2-phthalimidoacetamide (7.5 g), m.p. 250° C., is thereby obtained.

2-Bromo-N-methyl-N-phenylacetamide may be prepared according to the method described by C. A. BISCHOFF, Chem. Ber., 34, 2125 (1901).

EXAMPLE 16

Using a procedure similar to that described in Example 11, but starting with tert-butyl 2-[2-amino-N-( 2-methoxyphenyl)acetamido]acetate (4.2 g) and 3-methylphenyl isocyanate (1.9 g), and after recrystallisation in ethyl acetate, tert-butyl 2-{N-(2-methoxyphenyl)-2-[3-(3-methylphenyl)ureido]acetamido} acetate (3 g), m.p. 171° C., is obtained.

tert-Butyl 2-[2-amino-N-(2-methoxyphenyl)acetamido] acetate may be prepared in a manner similar to that described in Example 1 for the preparation of tert-butyl 2-[2-amino-N-(3-chlorophenyl)acetamido]acetate, but starting with tert-butyl 2-[N-(2-methoxyphenyl)- 2-phthalimidoacetamido]acetate (8.4 g) and hydrazine hydrate (3 g) and working at a temperature in the region of 20° C. tert-Butyl 2-[2-ammino-N-(2-methoxyphenyl)acetamido]acetate (4.2 g) is thereby obtained in the form of an oil, which is used without further purification in the subsequent syntheses.

tert-Butyl 2-[N-(2-methoxyphenyl)-2-phthalimidoacetamido] acetate may be prepared in a manner similar to that described in Example 1 for the preparation of tert-butyl 2-[N-(3-chlorophenyl)-2-phthalimidoacetamido] acetate, but starting with tert-butyl 2-[(2-methoxyphenyl)amino]acetate (6.4 g), triethylamine (2.7 g) and 2-phthalimidoacetyl chloride (6 g). After recrystallisation in diisopropyl ether, tert-butyl 2-[N-(2-methoxyphenyl)-2-phthalimidoacetamido] acetate (8.4 g), m.p. 144° C., is thereby obtained.

tert-Butyl 2-[(2-methoxyphenyl)amino]acetate may be prepared in a manner similar to that described in Example 1 for the preparation of tert-butyl 2-[(3-chlorophenyl)amino] acetate, but starting with 2-methoxyaniline (7.4 g) and tert-butyl bromoacetate (5.9 g). tert-Butyl 2-[(2-methoxyphenyl)amino]acetate (6.4 g) is thereby obtained in the form of an oil, which is used without further purification in the subsequent syntheses.

EXAMPLE 17 tert-Butyl 2-[(4-nitrophenyl)amino]acetate (4.5 g) is added at a temperature in the region of 20° C. to a suspension, maintained under an argon atmosphere, of 2-[3-(3-methylphenyl)ureido]acetic acid (3.7 g) in 1,2-dichloroethane (230 cc). The reaction mixture is heated with stirring to reflux of the solvent. Sulphinyl chloride (2.12 g) is then added dropwise while refluxing is maintained. When the addition is complete, heating to reflux is continued for 10 minutes and the reaction mixture is then cooled to a temperature in the region of 10° C. and poured into a solution of sodium hydrogen carbonate (15 g) in water (300 cc). The aqueous phase is separated after settling has taken place and re-extracted with 1,2-dichloroethane (2×50 cc). The organic phases are combined, washed with water (3×20 cc), dried over magnesium sulphate, filtered and then concentrated to dryness under reduced pressure (2.7 kPa) at 40° C. The residue is purified by chromatography on silica (0.063– 0.2 mm) (200 g) contained in a column 3.5 cm in diameter [eluent: cyclohexane/ethyl acetate (50:50 by volume)], collecting 30-cc fractions. Fractions 16–25 are combined and concentrated to dryness under reduced pressure (2.7 kPa) at 40° C. After recrystallisation in ethyl acetate, tert-butyl 2-{2-[3-(3-methylphenyl)ureido] -N-(4-nitrophenyl)acetamido}acetate (2.9 g), m.p. 152° C., is obtained.

tert-Butyl 2-[(4-nitrophenyl)amino]acetate may be prepared in the following manner: a mixture of 4-nitroaniline (6.9 g), tert-butyl bromoacetate (19.5 g) and sodium hydrogen carbonate (9.24 g) is heated with stirring and under an argon atmosphere to a temperature of 160° C. for 2 hours 30 minutes, then cooled to a temperature in the region of 20° C. and poured into a mixture of water (150 cc) and ethyl acetate (150 cc). The aqueous phase is separated after settling has taken place and re-extracted with ethyl acetate (3×50 cc). The organic phases are combined, washed with water (3×20 cc), dried over magnesium sulphate, filtered and then concentrated to dryness under reduced pressure (2.7 kPa) at 40° C. After recrystallisation in a mixture of ethyl acetate and cyclohexane (50:50 by volume), tert-butyl 2-[(4-nitrophenyl)amino]acetate (7.7 g), m p 124° C. is obtained.

2-[3-(3-Methylphenyl)ureido]acetic acid may be prepared in the following manner: 3-methylphenyl isocyanate (13.3 g) is added at a temperature in the region of 20° C. to a solution of glycine (7.5 g) and sodium hydrogen carbonate (8.4 g) in water (250 cc). The reaction mixture is stirred for 18 hours at a temperature in the region of 20° C. and the insoluble product is then separated by filtration and washed with water (2×30 cc) and then with ethyl acetate (2×30 cc). The filtrates are combined and the aqueous phase is separated after settling has taken place and acidified with 5N aqueous hydrochloric acid solution to a pH in the region of 1. The solid formed is separated by filtration, washed with water (2×30 cc) and then with ethyl acetate (2×30 cc) and dried in the air. 2-[3-(3-Methylphenyl)ureido]acetic acid (16.3 g), m.p. 225° C., is thereby obtained.

EXAMPLE 18

Using a procedure similar to that described in Example 17, but starting with 2-[3-(3-methylphenyl)ureido] acetic acid (1.04 g), tert-butyl 2-[(2,3-dichlorophenyl)amino] acetate (1.4 g) and sulphinyl chloride (0.6 g), and after recrystallisation in acetonitrile, tert-butyl 2-{N-(2,3-dichlorophenyl)-2-[3 -(3-methylphenyl)ureido]acetamido}acetate (0.3 g), m.p. 135° C., is obtained.

tert-Butyl 2-[(2,3-dichlorophenyl)amino]acetate may be prepared in the following manner: sodium hydrogen carbonate (16.8 g) and then a solution of tert-butyl bromoacetate (39 g) in acetonitrile (50 cc) are added at a temperature in the region of 20° C. to a solution of 2,3-dichloroaniline (32.4 g) in acetonitrile (100 cc). The reaction mixture is stirred under reflux for 48 hours and then cooled to a temperature in the region of 20° C. The insoluble product is separated by filtration and washed with acetonitrile (50 cc). The filtrates are combined and concentrated to dryness under reduced pressure (2.7 kPa) at 40° C. The residue is purified by chromatography on silica (0.063–0.2 mm) (300 g) contained in a column 4 cm in diameter [eluent: cyclohexane/ ethyl acetate (90:10 by volume)], collecting 50-cc fractions. The fractions containing only the desired product are combined and concentrated to dryness under reduced pressure (2.7 kPa) at 40° C. tert-Butyl 2-[(2,3-dichlorophenyl)amino] acetate (33 g) is thereby obtained in the form of an oil, which is used without further purification in the subsequent syntheses.

EXAMPLE 19

Using a procedure similar to that described in Example 17, but starting with 2-[3-(3-methylphenyl)ureido] acetic acid (3.12 g), tert-butyl 2-[(2-bromophenyl)amino] acetate (4.3 g) and sulphinyl chloride (2 g), and after recrystallisation in a mixture of diisopropyl ether and acetonitrile (80:20 by volume), tert-butyl 2-{N-(2-bromophenyl)-2-[3-(3-methylphenyl)ureido] acetamido}acetate (0.6 g), m.p. 158° C., is obtained.

tert-Butyl 2-[(2-bromophenyl)amino]acetate may be prepared in a manner similar to that described in Example 18 for the preparation of tert-butyl 2-[(2,3-dichlorophenyl)amino]acetate, but starting with 2-bromoaniline (34.4 g), sodium hydrogen carbonate (8.4 g) and tert-butyl bromoacetate (19.5 g). tert-Butyl 2-[(2-bromophenyl)amino]acetate (17.4 g) is thereby obtained in the form of an oil, which is used without further purification in the subsequent syntheses.

EXAMPLE 20

Using a procedure similar to that described in Example 17, but starting with 2-[(3-methylphenyl)ureido] acetic acid (2.08 g), tert-butyl 2-[(3-trifluoromethylthiophenyl)amino] acetate (3.07 g) and sulphinyl chloride (1.3 g), and after recrystallisation in diisopropyl ether, tert-butyl 2-{2-[3-(3-methylphenyl)ureido] -N-(3-trifluoromethylthiophenyl)acetamido} acetate (0.8 g), m.p. 112° C., is obtained.

tert-Butyl 2-[(3-trifluoromethylthiophenyl)amino] acetate may be prepared in a manner similar to that described in Example 18 for the preparation of tert-butyl 2-[(2,3-dichlorophenyl)amino]acetate, but starting with 3-trifluoromethylthioaniline (19.3 g), sodium hydrogen carbonate (8.4 g) and tert-butyl bromoacetate (19.5 g). tert-Butyl 2-[(3-trifluoromethylthiophenyl)amino] acetate (25.5 g) is thereby obtained in the form of an oil, which is used without further purification in the subsequent syntheses.

EXAMPLE 21

Methyl hydrazine (2.13 g) is added at a temperature in the region of 0° C. to a solution of tert-butyl 2-[N-(2-methylphenyl)-2-phthalimidoacetamido]acetate (5.5 g) in dichloromethane (90 cc). The reaction mixture is stirred for 30 hours at a temperature in the region of 20° C. and then for 1 hour under reflux. After cooling, water (100 cc) is added, the mixture is stirred and the aqueous phase is separated after settling has taken place and re-extracted with dichloromethane (2×60 cc). The organic phases are combined, washed with water (2×15 cc), dried over magnesium sulphate, filtered and then concentrated to dryness under reduced pressure (2.7 kPa) at 40° C. tert-Butyl 2-[2-amino-N-(2-methylphenyl)acetamido] acetate is thereby obtained in the form of an oil, which is dissolved in anhydrous tetrahydrofuran (40 cc). 3-Methylphenyl isocyanate (1.77 g) is added to this solution and the reaction mixture is then stirred for 1 hour at a temperature in the region of 20° C. and concentrated to dryness under reduced pressure (2.7 kPa) at 40° C. After recrystallisation in petroleum ether, tert-butyl 2-{N-(2-methylphenyl)-2-[3-(3-methylphenyl)ureido]acetamido} acetate (1.05 g), m.p. 133° C., is obtained.

tert-Butyl 2-[N-(2-methylphenyl)-2-phthalimidoacetamido] acetate may be prepared in a manner similar to that described in Example 1 for the preparation of tert-butyl 2-[N-(3-chlorophenyl)-2-phthalimidoacetamido] acetate, but starting with tert-butyl 2-[(2-methylphenyl)amino]acetate (5.2 g), triethylamine (2.6 g) and 2-phthalimidoacetyl chloride (5.3 g). After recrystallisation in ethyl acetate, tert-butyl 2-[N-(2-methylphenyl)-2-phthalimidoacetamido] acetate (5.5 g), m.p. 140° C., is thereby obtained.

tert-Butyl 2-[(2-methylphenyl)amino]acetate may be prepared in a manner similar to that described in Example 18 for the preparation of tert-butyl 2-[(2,3-dichlorophenyl)amino]acetate, but starting with 2-methylaniline (6.4 g), sodium hydrogen carbonate (2.5 g) and tert-butyl bromoacetate (5.85 g). tert-Butyl 2-[(2-methylphenyl)amino]acetate (5.2 g) is thereby obtained in the form of an oil, which is used in the subsequent syntheses.

EXAMPLE 22

The procedure used is similar to that described in Example 17, but starting with tert-butyl 2-[(4-chlorophenyl)amino]acetate (1.8 g), 2-[3 -(3-methylphenyl)-ureido]acetic acid (1.56 g) and thionyl chloride (0.89 g). The product obtained is purified by chromatography on silica (0.04–0.063 mm) (60 g) contained in a column 2.5 cm in diameter [eluent: cyclohexane/ethyl acetate (80:20 by volume)], using an excess pressure of nitrogen of 40 kPa and collecting 20-cc fractions. Fractions 21 to 25 are combined and concentrated to dryness under reduced pressure (2.7 kPa) at 40° C. After crystallisation in acetonitrile, tert-butyl 2-{N-(4-chlorophenyl)-2-[ 3-(3-methylphenyl)ureido] acetamido}acetate (0.5 g), m.p. 125° C., is obtained.

tert-Butyl 2-[(4-chlorophenyl)amino]acetate may be prepared in the following manner: tert-Butyl bromoacetate (9.7 g) is added to a solution of 4-chloroaniline (12.7 g) in acetonitrile (100 cc), and the mixture is stirred under reflux for 3 hours. The insoluble product is separated by filtration and the filtrate is concentrated to dryness under reduced pressure (2.7 kPa) at 40° C. The product obtained is purified by chromatography on silica (0.065–0.2 mm) (150 g) contained in a column 2 cm in diameter [eluent: cyclohexane/ ethyl acetate (70:30 by volume)], collecting 20-cc fractions. After concentration under reduced pressure (2.7 kPa) at 40° C., tert-butyl 2-[(4-chlorophenyl)amino]acetate (11.9 g) is obtained in the form of an oil, which is used without further purification in the subsequent syntheses.

EXAMPLE 23

The procedure used is similar to that described in Example 1, but starting with tert-butyl 2-[2-amino-N-(3-methoxyphenyl)acetamido]acetate (2.3 g) and 3-methylphenyl isocyanate (1.1 g). The product obtained is purified by chromatography on silica (0.04–0.063 mm) (150 g) contained in a column 3.5 cm in diameter [eluent: cyclohexane/ ethyl acetate (70:30 by volume)], using an excess pressure of nitrogen of 40 kPa and collecting 20-cc fractions. Fractions 10 to 16 are combined and concentrated to dryness under reduced pressure (2.7 kPa) at 40° C. After recrystallisation in diisopropyl ether, tert-butyl 2-{N-(3-methoxyphenyl)-2-[3-(3-methylphenyl)ureido]acetamido} acetate (2.2 g), m.p. approximately 60° C., is obtained.

tert-Butyl 2-[2-amino-N-(3-methoxyphenyl)acetamido] acetate may be prepared in a manner similar to that described in Example 1 for the preparation of tert-butyl 2-[2-amino-N-(3-chlorophenyl)acetamido]acetate, but starting with tert-butyl 2-[N-(3-methoxyphenyl)- 2-phthalimidoacetamido]acetate (3.4 g) and hydrazine hydrate (0.8 g). tert-Butyl 2-[2-amino-N-( 3-methoxyphenyl)acetamido]acetate (2.0 g) is thereby obtained in the form of an oil, which is used without further purification in the subsequent syntheses.

tert-Butyl 2-[N-(3-methoxyphenyl)-2-phthalimidoacetamido] acetate may be prepared in the following manner: phthalimide potassium salt (7.5 g) is added to a solution of tert-butyl 2-[2-chloro-N-( 3-methoxyphenyl)acetamido]acetate (6.3 g) in dimethylformamide (100 cc). The mixture is stirred at a temperature in the region of 100° C. for 5 hours and then poured into water (1000 cc). The insoluble product is separated by filtration, washed with water (3×60 cc) and dried in the air. After recrystallisation in diisopropyl ether, tert-butyl 2-[N-(3-methoxyphenyl)- 2-phthalimidoacetamido]acetate (6.7 g), m p 138° C. is obtained.

tert-Butyl 2-[2-chloro-N-(3-methoxyphenyl)acetamido] acetate may be prepared in the following manner: chloroacetyl chloride (5.7 g) is added to a solution, maintained at a temperature in the region of 15° C., of tert-butyl 2-[(3-methoxyphenyl)amino]acetate (7.9 g) and triethylamine (6.7 g) in 1,2-dichloroethane (50 cc). The mixture is stirred for 6 hours at a temperature in the region of 60° C. After cooling, the mixture is washed with water (3×100 cc). The organic phase is dried over magnesium sulphate and concentrated to dryness under reduced pressure (2.7 kPa) at 40° C. After recrystallisation in diisopropyl ether, tert-butyl 2-[2-chloro-N-(3-methoxyphenyl)acetamido]acetate (6.3 g), m.p. 110° C., is thereby obtained.

tert-Butyl 2-[(3-methoxyphenyl)amino]acetate may be prepared in a manner similar to that described in Example 1 for the preparation of tert-butyl 2-[(3-chlorophenyl)amino] acetate, but starting with 4-methoxyaniline (12.4 g) and tert-butyl bromoacetate (9.75 g). The product obtained is purified by chromatography on silica (0.063–0.200 mm) (200 g) contained in a column 7.0 cm in diameter (eluent: dichloromethane), collecting 60-cc fractions. Fractions 10 to 20 are combined and concentrated to dryness under reduced pressure (2.7 kPa) at 40° C. tert-Butyl 2-[(3-methoxyphenyl)amino]acetate (9.8 g) is thereby obtained in the form of an oil, which is used without further purification in the subsequent syntheses.

EXAMPLE 24

3-Methylthioaniline (0.83 g) is added to a solution of tert-butyl 2-{N-(4-dimethylaminophenyl)- 2-[(1-imidazolyl)carboxamido]acetamido}acetate (1.2 g) in toluene (30 cc), and the mixture is stirred under reflux for 4 hours. After cooling, ethyl acetate (30 cc) is added and the solution obtained is then washed successively with water (30 cc), with 1N aqueous hydrochloric acid solution (2×30 cc), with saturated aqueous sodium hydrogen carbonate solution (2×30 cc) and with saturated aqueous sodium chloride solution (30 cc). The organic phase is dried over magnesium sulphate and then concentrated to dryness under reduced pressure (2.7 kPa) at 40° C. The residue is purified by chromatography on silica (0.065–0.200 mm) (100 g) contained in a column 2.7 cm in diameter (eluent: methylene chloride), collecting 70-cc fractions. Fractions 24 to 32 are combined and concentrated to dryness under reduced pressure (2.7 kPa) at 40° C. After recrystallisation in acetonitrile, tert-butyl 2-{N-(4-dimethylaminophenyl)- 2-[3-(3-methylthiophenyl)ureido]acetamido}acetate (0.40 g), m.p. 160° C., is obtained.

tert-Butyl 2-{N-(4-dimethylaminophenyl)- 2-[(1-imidazolyl)carboxamido]acetamido}acetate may be prepared in the following manner: a solution of tert-butyl 2-[2-amino-N-(4-dimethylaminophenyl)acetamido]acetate (1.2 g) in anhydrous tetrahydrofuran (15 cc) is added to a solution of N,N'-carbonyldiimidazole (0.58 g) in anhydrous tetrahydrofuran (20 cc). The solution is stirred for 3 hours at a temperature in the region of 20° C. and then concentrated to dryness under reduced pressure (2.7 kPa) at 40° C. The residue is dissolved in ethyl acetate (30 cc) and the solution obtained is washed successively with water (4×20 cc) and with saturated aqueous sodium chloride solution (25 cc). The organic phase is dried over magnesium sulphate and then concentrated to dryness under reduced pressure (2.7 kPa) at 40° C. After recrystallisation in ethyl acetate, tert-butyl 2-{N-(4-dimethylaminophenyl)- 2-[(1-imidazolyl)carboxamido]acetamido}acetate (1.2 g), m.p. 110° C., is obtained.

EXAMPLE 25

Triethylamine (0.55 g) and then 2-indole-carbonyl chloride (0.9 g) dissolved in 1,2-dichloroethane (35 cc) are added to a solution, stirred at a temperature in the region of 25° C., of tert-butyl 2-[2-amino-N-(4-dimethylaminophenyl)acetamido]acetate (1.1 g) in 1,2-dichloroethane (35 cc). The reaction mixture is stirred for 18 hours at a temperature in the region of 25° C. Dichloromethane (250 cc) is then added, followed by saturated aqueous sodium hydrogen carbonate solution (125 cc). The organic phase is washed with water (2×125 cc), dried over magensium sulphate and concentrated to dryness under reduced pressure (2.7 kPa) at 40° C. After recrystallisation in ethyl acetate N-[N-(4-dimethylaminophenyl)-N-(tert-butoxycarbonylmethyl)carbamoylmethyl] -2-indole-carboxamide (0.35 g), m.p. 230° C., is obtained.

2-Indolecarbonyl chloride may be prepared in the following manner: dimethylformamide (0.1 cc) and then oxalyl dichloride (1.5 g) dissolved in anhydrous diethyl ether (10 cc) are added to a suspension of 2-indolecarboxylic acid (1.85 g) in anhydrous diethyl ether (40 cc) at a temperature in the region of 5° C. The reaction mixture is stirred at a temperature in the region of 25° C. for 2 hours. The ether phase is concentrated to dryness under reduced pressure (2.7 kPa) at 30° C. 2-Indolecarbonyl chloride (1.8 g), m.p. 120° C., is thereby obtained.

EXAMPLE 26

1N aqueous sodium hydroxide solution (5 cc) is added to a solution of ethyl 3-{3-[N-(3-methoxyphenyl)-N-(N-methyl-N-phenylcarbamoylmethyl)carbamoylmethyl] ureido}benzoate (1.85 g) in a water/tetrahydrofuran/dioxane (30:40:30 by volume) mixture (75 cc). The mixture is stirred for 16 hours at a temperature in the region of 25° C. and then concentrated to approximately 40 cc under reduced pressure (2.7 kPa) at 10° C. The solution obtained is diluted with water (50 cc), washed with ethyl acetate (2×50 cc), acidified to pH 3 with 4N hydrochloric acid solution and extracted with ethyl acetate (2×30 cc). The organic phases are combined, washed with water (30 cc), dried over magnesium sulphate and concentrated to dryness under reduced pressure (2.7 kPa) at 30° C. After recrystallisation in an acetonitrile/dimethylformamide (90:10 by volume) mixture, 3-{3-[N-(3-methoxyphenyl)-N-(N-methyl-N-phenylcarbamoylmethyl)carbamoylmethyl]ureido} benzoic acid (0.9 g), m.p. 222° C., is obtained, Ethyl 3-{3-[N-(3-methoxyphenyl)-N-(N-methyl-N-phenylcarbamoylmethyl)carbamoylmethyl] ureido}benzoate may be prepared in the following manner: ethyl 3-aminobenzoate (0.94 g) is added to a solution of 2-[N-(3-methoxyphenyl)isocyanatoacetamido] -N-methyl-N-phenyl-acetamide (2.1 g) in anhydrous tetrahydrofuran (80 cc). The mixture is stirred at a temperature in the region of 25° C. for 18 hours and then concentrated to dryness under reduced pressure (2.7 kPa) at 40° C. The crude product obtained is purified by chromatography on silica (0.065–0.20 mm) (80 g) contained in a column 2.5 cm in diameter [eluent: methanol/dichloromethane (20:80 by volume)], using an excess pressure of 40 kPa of nitrogen and collecting 80-cc fractions. Fractions 8 to 11 are combined and concentrated to dryness under reduced pressure (2.7 kPa) at 40° C. Ethyl 3-{3-[N-( 3-methoxyphenyl)-N-(N-methyl-N-phenylcarbamoylmethyl)carbamoylmethyl] ureido}benzoate (1.9 g) is thereby obtained in the form of a meringue-like product, which is used without further purification in the subsequent syntheses.

2-[N-(3-Methoxyphenyl)isocyanatoacetamido] -N-methyl-N-phenylacetamide may be prepared in the following manner: isocyanatoacetyl chloride (0.87 g) dissolved in anhydrous tetrahydrofuran (10 cc) is added to a solution, maintained at a temperature in the region of 5° C., of 2-[(3-methoxyphenyl)amino] -N-methyl-N-phenylacetamide (1.55 g) and pyridine (0.5 g) in anhydrous tetrahydrofuran (30 cc), and the mixture is then stirred for 3 hours at a temperature in the region of 25° C. The insoluble product is separated by filtration and the filtrate is concentrated to dryness under reduced pressure (2.7 kPa) at 30° C. 2-[N-(3-Methoxyphenyl)isocyanatoacetamido] -N-methyl-N-phenylacetamide (1.9 g) is thereby obtained in the form of an oil, which is used without further purification in the subsequent syntheses.

2-[(3-Methoxyphenyl)amino]-N-methyl-N-phenyl-acetamide may be prepared in the following manner: 2N aqueous sodium hydroxide solution (14.2 cc) is added at a temperature in the region of 20° C. to a solution of 2-[N-(3-methoxyphenyl)trifluoroacetamido]-N-methyl-N-phenylacetamide (5.2 g) in ethanol (80 cc). The reaction mixture is stirred under reflux for 5 minutes and the ethanol is then removed by evaporation under reduced pressure (2.7 kPa) at 40° C. Ethyl acetate (150 cc) is added to the residue and the aqueous phase is separated after settling has taken place. The organic phase is washed with water (5×20 cc), dried over magnesium sulphate, filtered and then concentrated to dryness under reduced pressure (2.7 kPa) at 40° C. The residual oil is purified by chromatography on silica (0.063–0.2 mm) (100 g) contained in a column 2.5 cm in diameter (eluent: dichloromethane), collecting 20-cc fractions. The fractions containing only the desired product are combined and concentrated to dryness under reduced pressure (2.7 kPa) at 40° C. 2-[(3-Methoxyphenyl)amino]-N-methyl-N-phenylacetamide (2.5 g) is thereby obtained in the form of an oil, which is used without further purification in the subsequent syntheses.

2-[N-(3-Methoxyphenyl)trifluoroacetamido] -N-methyl-N-phenylacetamide may be prepared in the following manner: an oily suspension (50% by weight) (1.4 g) of sodium hydride is added at a temperature in the region of 10° C. to a solution, maintained under an argon atmosphere, of N-(3-methoxyphenyl)trifluoroacetamide (5 g) in anhydrous tetrahydrofuran (80 cc), and the suspension obtained is stirred for 30 minutes at a temperature in the region of 20° C. A solution of 2-bromo-N-methyl-N-phenylacetamide (7.9 g) in anhydrous tetrahydrofuran (50 cc) is then added and the mixture is heated to reflux with stirring for 5 hours. The reaction mixture is then cooled to a temperature in the region of 20° C. and poured into a mixture of water (100 cc) and ethyl acetate (150 cc). The aqueous phase is separated after settling has taken place and re-extracted with ethyl acetate (2×100 cc). The organic phases are combined, washed with water (3×100 cc), dried over magnesium sulphate, filtered and then concentrated to dryness under reduced pressure (2.7 kPa) at 40° C. The oil obtained is purified by chromatography on silica (0.063–0.2 mm) (100 g) contained in a column 3.5 cm in diameter (eluent: dichloromethane), collecting 20-cc fractions. The fractions containing only the desired product are combined and concentrated to dryness under reduced pressure (2.7 kPa) at 40° C. 2-[N-(3-Methoxyphenyl)trifluoroacetamido] -N-methyl-N-phenylacetamide (5.2 g) is thereby obtained in the form of an oil, which is used without further purification in the subsequent syntheses.

N-(3-Methoxyphenyl)trifluoroacetamide may be prepared in the following manner: trifluoroacetic anhydride (5.25 g) is added at a temperature in the region of −20° C. to an anhydrous solution of 3-methoxyaniline (3.1 g) in pyridine (25 cc). The reaction mixture is stirred for 30 minutes at a temperature in the region of −20° C. and then for 1 hour at a temperature in the region of 0° C. and poured into water (150 cc) cooled to a temperature in the region of 0° C. The insoluble oil is extracted with diethyl ether (200 cc) and the organic phase obtained is washed with 1N aqueous hydrochloric acid solution (2×30 cc) and then water (2×30 cc), dried over magnesium sulphate and concentrated to dryness under reduced pressure (2.7 kPa) at 30° C. N-(3-Methoxyphenyl)trifluoroacetamide (5.7 g) is thereby obtained in the form of an oil, which is used without further purification in the subsequent syntheses.

2-Bromo-N-methyl-N-phenylacetamide may be prepared in the following manner: triethylamine (11.1 g) and a solution of bromoacetyl bromide (20.4 g) in dichloromethane (10 cc) are added successively at a temperature in the region of −5° C. to a solution of N-methylaniline (10.7 g) in dichloromethane (65 cc). The suspension obtained is stirred for 2 hours at a temperature in the region of 20° C. and then treated with water (25 cc). The aqueous phase is separated after settling has taken place and re-extracted with dichloromethane (2×15 cc). The organic phases are combined, washed with water (3×25 cc), dried over magnesium sulphate, filtered and then concentrated to dryness under reduced pressure (2.7 kPa) at 40° C. The residual oil is treated with anhydrous diethyl ether (100 cc); the insoluble product is separated by filtration and washed with diethyl ether (3×15 cc). The filtrates are combined and concentrated to dryness under reduced pressure (2.7 kPa) at 40° C. 2-Bromo-N-methyl-N-phenylacetamide (20.5 g) is thereby obtained in the form of an oil, which is used without further purification in the subsequent syntheses.

Isocyanatoacetyl chloride may be prepared according to the method described by YOSHIO IWAKURA et al., J. Org. Chem. 30, 1158 (1965).

EXAMPLE 27

3-Methylphenyl isocyanate (1.2 g) is added at a temperature in the region of 20° C. to a solution of tert-butyl 2-{2-amino-N-[2-(3,3-dimethylpiperidino)-carbonylphenyl] acetamido}acetate (4.8 g) in anhydrous tetrahydrofuran (40 cc). The solution obtained is stirred for 4 hours at a temperature in the region of 20° C. and then concentrated to dryness under reduced pressure (2.7 kPa) at 40° C. The residual oil is purified by chromatography on silica (0.063–0.2 mm) (150 g) contained in a column 3.5 cm in diameter [eluent: dichloromethane/methanol (98:2 by volume)], collecting 50-cc fractions. The fractions containing only the desired product are combined and concentrated to dryness under reduced pressure (2.7 kPa) at 40° C. After recrystallisation in ethyl acetate, tert-butyl 2-{N-[2-(3,3-dimethylpiperidino)carbonylphenyl]-2-[3-(3-methylphenyl)ureido] acetamido}acetate (3.2 g), m.p. 207° C., is obtained.

tert-Butyl 2-{2-amino-N-[2-(3,3-dimethylpiperidino)carbonylphenyl] acetamido}acetate may be prepared in the following manner: hydrazine hydrate (1.9 g) is added to a solution of tert-butyl 2-{N-[2-(3,3-dimethylpiperidino)carbonylphenyl]-2-phthalimidoacetamido}acetate (6.3 g) in methanol (100 cc). The reaction mixture is heated to reflux for 4 hours and then concentrated to dryness under reduced pressure (2.7 kPa) at 40° C. The residual oil is dissolved in ethyl acetate (200 cc) and the solution obtained is treated with water (50 cc). The aqueous phase is separated after settling has taken place and then re-extracted with ethyl acetate (2×30 cc). The organic phases are combined, washed with water (2×30 cc), dried over magnesium sulphate, filtered and then concentrated to dryness under reduced pressure (2.7 kPa) at 40° C. tert-Butyl 2-{2-amino-N-[2-(3,3-dimethylpiperidino)carbonylphenyl] acetamido}acetate (4.8 g) is thereby obtained in the form of an oil, which is used without further purification in the subsequent syntheses.

tert-Butyl 2-{N-[2-(3,3-Dimethylpiperidino)carbonylphenyl] -2-phthalimidoacetamido}acetate may be prepared in the following manner: an oily suspension (50% by weight) (1.05 g) of sodium hydride is added at a temperature in the region of 10° C. to a solution, maintained under an argon atmosphere, of N-[2-(3,3-dimethylpiperidino)carbonylphenyl] -2-phthalimidoacetamide (8.4 g) dissolved in anhydrous tetrahydrofuran (100 cc), and the mixture obtained is stirred for 1 hour at a temperature in the region of 20° C. A solution of tert-butyl bromoacetate (4.5 g) in anhydrous tetrahydrofuran (25 cc) is then added and the mixture is stirred for a further 3 hours at a temperature in the region of 20° C. and then for 4 hours under reflux of the solvent. The reaction mixture is then poured into a mixture, cooled to a temperature in the region of 0° C., of distilled water (30 cc) and ethyl acetate (200 cc). The aqueous phase is separated after settling has taken place and re-extracted with ethyl acetate (2×20 cc). The organic phases are combined, washed with water (3×25 cc), dried over magnesium sulphate, filtered and then concentrated to dryness under reduced pressure (2.7 kPa) at 40° C. tert-Butyl 2-{N-[2-(3, 3-dimethylpiperidino)carbonylphenyl] -2phthalimidoacetamido} acetate (6.5 g) is thereby obtained in the form of an amorphous solid, which is used without further purification in the subsequent syntheses.

N-[2-(3,3-Dimethylpiperidino)carbonylphenyl]-2-phthalimidoacetamide may be prepared in the following manner: to a solution, maintained under an argon atmosphere, of 2-(3,3-dimethylpiperidino)carbonylaniline (7 g) in dichloromethane (150 cc), triethylamine (3.3 g) is added, and a solution of 2-phthalimidoacetyl chloride (6.8 g) in dichloromethane (100 cc) is then added while the temperature is maintained at 20° C. The solution obtained is stirred for 3 hours at a temperature in the region of 20° C. and then treated with water (100 cc) and dichloromethane (150 cc). The aqueous phase is separated after settling has taken place and re-extracted with dichloromethane (2×50 cc). The organic phases are combined, washed with water (3×75 cc), dried over magnesium sulphate, filtered and then concentrated to dryness under reduced pressure (2.7 kPa) at 40C [sic]. After recrystallisation in ethyl acetate, N-[2-(3,3-dimethylpiperidino)carbonylphenyl]-2-phthalimidoacetamide (10.4 g), m.p. 158° C. is thereby obtained.

2-(3,3-Dimethylpiperidino)carbonylaniline may be prepared in the following manner: 2-[(3,3-dimethylpiperidino)carbonyl]nitrobenzene (16.7 g) is added to a suspension of stannous chloride dihydrate (51.6 g) in 6N aqueous hydrochloric acid solution (64 cc) while the temperature is maintained in the region of 45° C. The reaction mixture is then heated to a temperature in the region of 85° C. for 1 hour 30 minutes, thereafter cooled to a temperature in the region of 20° C. and poured into a mixture, cooled to a temperature in the region of 0° C., of water (300 cc) and dichloromethane (250 cc). The mixture is alkalinised by adding 11N aqueous ammonia solution to a pH in the region of 9. The aqueous phase is separated after settling has taken place and re-extracted with dichloromethane (2×100 cc). The organic phases are combined, washed with water (4×100 cc), dried over magnesium sulphate, filtered and then concentrated to dryness under reduced pressure (2.7 kPa) at 40° C. 2-(3,3-Dimethylpiperidino)carbonylaniline (14.2 g) is thereby obtained in the form of an oil, which is used without further purification in the subsequent syntheses.

2-[(3,3-Dimethylpiperidino)carbonyl]nitrobenzene may be prepared in the following manner: a solution of 2-nitrobenzoyl chloride (13.6 g) in dichloromethane (25 cc) is added at a temperature in the region of 15° C. to a solution of 3,3-dimethylpiperidine (7.9 g) and triethylamine (7.7 g) in dichloromethane (100 cc). The suspension is stirred for 2 hours at a temperature in the region of 20° C. and then poured into a mixture of water (75 cc) and dichloromethane (100 cc). The aqueous phase is separated after settling has taken place and re-extracted with dichloromethane (2×50 cc). The organic phases are combined, washed with water (3×30 cc), then with 1N aqueous hydrochloric acid solution (30 cc) and with water (3×25 cc), dried over magnesium sulphate, filtered and then concentrated to dryness under reduced pressure (2.7 kPa) at 40° C. 2-[(3,3-Dimethylpiperidino)carbonyl]nitrobenzene (16.8 g) is thereby obtained in the form of an oil, which is used without further purification in the subsequent syntheses.

EXAMPLE 28

Using a procedure similar to that described in Example 27, but starting with tert-butyl 2-{2-amino-N-[2-(N-methylanilino)carbonylphenyl] acetamido}acetate (2.5 g) and 3-methylphenyl isocyanate (0.83 g), and after recrystallisation in ethyl acetate, tert-butyl 2-{N-[2-(N-methylanilino)carbonylphenyl]-2-[3-(3-methylphenyl)ureido] acetamido}acetate (1.9 g), m.p. 145° C., is obtained.

tert-Butyl 2-{2-amino-N-[2-(N-methylanilino)carbonylphenyl] acetamido}acetate may be prepared in a manner similar to that described in Example 27 for the preparation of tert-butyl 2-{2-amino-N-[2-(3,3-dimethylpiperidino)carbonylphenyl] acetamido}acetate, but starting with tert-butyl 2-{N-[2-(N-methylanilino)carbonylphenyl] -2-phthalimidoacetamido}acetate (3.3 g) and hydrazine hydrate (0.93 g). tert-Butyl 2-{2-amino-N-[2 -(N-methylanilino)carbonylphenyl]acetamido}acetate (2.5 g) is thereby obtained in the form of an oil, which is used without further purification in the subsequent syntheses.

tert-Butyl 2-{N-[2-(N-methylanilino)carbonylphenyl]-2-phthalimidoacetamido} acetate may be prepared in a manner similar to that described in Example 27 for the preparation of tert-butyl 2-{N-[2-(3,3-dimethylpiperidino)carbonylphenyl] -2-phthalimidoacetamido} acetate, but starting with N-[2-(N-methylanilino)carbonylphenyl] -2-phthalimidoacetamide (8.3 g), an oily suspension (50% by weight) (1.1 g) of sodium hydride and tert-butyl bromoacetate (4.5 g). After recrystallisation in ethyl acetate, 2-{N-[2-(N-methylanilino)carbonylphenyl] -2-phthalimidoacetamido}acetate (3.4 g), m.p. 160° C., is thereby obtained.

N-[2-(N-Methylanilino)carbonylphenyl)-2-phthalimidoacetamide may be prepared in a manner similar to that described in Example 27 for the preparation of N-[2-(3,3-dimethylpiperidino)carbonylphenyl] -2-phthalimidoacetamide, but starting with 2-(N-methylanilino)carbonylaniline (6.8 g), triethylamine (3.3 g) and 2-phthalimidoacetyl chloride (6.8 g). After recrystallisation in ethyl acetate, N-[2-(N-methylanilino)carbonylphenyl]-2-phthalimidoacetamide (10.8 g), m.p. 138° C., is thereby obtained.

2-(N-Methylanilino)carbonylaniline may be prepared in a manner similar to that described in Example 27 for the preparation of 2-(3,3-dimethylpiperidino)carbonylaniline, but starting with stannous chloride dihydrate (50 g), 6N aqueous hydrochloric acid solution (70 cc) and 2-[(N-methylanilino)carbonyl] nitrobenzene (17.5 g). After recrystallisation in diisopropyl ether, 2-(N-methylanilino)carbonylaniline (10.3 g), m.p. 127° C., is thereby obtained.

2-[(N-Methylanilino)carbonyl]nitrobenzene may be prepared in a manner similar to that described in Example 27 for the preparation of 2-[(3,3-dimethylpiperidino)carbonyl] nitrobenzene, but starting with N-methylaniline (7.2 g), triethylamine (7.7 g) and 2-nitrobenzoyl chloride (13.6 g). 2-[(N-Methylanilino)carbonyl] nitrobenzene (17.7 g) is thereby obtained in the form of an oil, which is used without further purification in the subsequent syntheses.

EXAMPLE 29

Using a procedure similar to that described in Example 27, but starting with tert-butyl 2-{2-amino-N-[2 -(1,2,3,4-tetrahydro-1-quinolyl)carbonylphenyl]acetamido} acetate (2 g) and 3-methylphenyl isocyanate (0.63 g), and after recrysallisation in ethyl acetate, tert-butyl 2-{2-[3-(3-methylphenyl)ureido]-N-[2-(1,2,3,4-tetrahydro-1 -quinolyl)carbonylphenyl]acetamido} acetate (1.2 g), m.p. 160° C., is obtained.

tert-Butyl 2-{2-amino-N-[2-(1,2,3,4-tetrahydro-1-quinolyl)carbonylphenyl] acetamido}acetate may be prepared in a manner similar to that described in Example 27 for the preparation of tert-butyl 2-{2-amino-N-[2-(3,3-dimethylpiperidino)carbonylphenyl] acetamido}acetate, but starting with tert-butyl 2-{2-phthalimido-N-[2-(1,2,3,4-tetrahydro-1-quinolyl)carbonylphenyl] acetamido}acetate (4.4 g) and hydrazine hydrate (1.2 g). tert-Butyl 2-{2-amino-N-[2-(1,2,3,4-tetrahydro-1-quinolyl)carbonylphenyl] acetamido}acetate (2.1 g) is thereby obtained in the form of an oil, which is used without further purification in the subsequent syntheses.

tert-Butyl 2-{2-phthalimido-N-[2-(1,2,3,4-tetrahydro-1-quinolyl)carbonylphenyl] acetamido}acetate may be prepared in a manner similar to that described in Example 27 for the preparation of tert-butyl 2-{N-[2-(3,3-dimethylpiperidino)carbonylphenyl]-2-phthalimidoacetamido} acetate, but starting with 2-phthalimido-N-[2-(1,2,3,4-tetrahydro-1-quinolyl)carbonylphenyl ]acetamide (31.5 g), an oily suspension (50% by weight) (3.75 g) of sodium hydride and tert-butyl bromoacetate ( 16.1 g). After recrystallisation in ethyl acetate, tert-butyl 2-{2-phthalimido-N-[2-(1,2,3,4-tetrahydro-1 -quinolyl)carbonylphenyl]acetamido} acetate (26.5 g), m.p. 150° C., is thereby obtained.

2-Phthalimido-N-[2-(1,2,3,4-tetrahydro-1-quinolyl)carbonylphenyl] acetamide may be prepared in a manner similar to that described in Example 27 for the preparation of 2-phthalimido-N-[2-(3,3-dimethylpiperidino)carbonylphenyl] acetamide, but starting with 2-(1,2,3,4-tetrahydro-1-quinolyl)carbonylaniline (20.2 g), triethylamine (9.1 g) and 2-phthalimidoacetyl chloride (19.7 g). After recrystallisation in ethyl acetate, 2-phthalimido-N-[2-(1,2,3,4-tetrahydro-1-quinolyl)carbonylphenyl] acetamide (31.6 g), m.p. 130° C., is thereby obtained.

2-(1,2,3,4-Tetrahydro-1-quinolyl)carbonylaniline may be prepared in a manner similar to that described in Example 27 for the preparation of 2-(3,3-dimethylpiperidino)carbonylaniline, but starting with stannous chloride dihydrate (114 g), 6N aqueous hydrochloric acid solution (140 cc) and 2-[(1, 2,3,4-tetrahydro-1-quinolyl)carbonyl] nitrobenzene (39.7 g). After recrystallisation in ethyl acetate, 2-(1,2,3,4-tetrahydro-1-quinolyl)carbonylaniline (20.2 g), m.p. 102° C., is thereby obtained.

2-[(1,2,3,4-Tetrahydro-1-quinolyl)carbonyl]nitrobenzene may be prepared in a manner similar to that described in Example 27 for the preparation of 2-[(3,3-dimethylpiperidino)carbonyl]nitrobenzene, but starting with 1,2,3,4-tetrahydroquinoline (20 g), triethylamine (16.5 g) and 2-nitrobenzoyl chloride (29.7 g). After recrystallisation in ethyl acetate, 2-[(1,2,3,4-tetrahydro-1-quinolyl)carbonyl]nitrobenzene (39.7 g), m.p. 155° C., is thereby obtained.

EXAMPLE 30

3-Methylphenyl isocyanate (1.07 g) is added at a temperature in the region of 20° C. to a solution of tert-butyl 2-[2-amino-N-(2-anilinophenyl)acetamido]acetate (2.6 g) in anhydrous tetrahydrofuran (20 cc). The solution obtained is stirred for 2 hours at a temperature in the region of 20° C. and then concentrated to dryness under reduced pressure (2.7 kPa) at 40° C. The residual oil is purified by chromatography on silica (0.063–0.2 mm) (150 g) contained in a column 2 cm in diameter [eluent: cyclohexane/ethyl acetate (50:50 by volume)], collecting 20-cc fractions. The fractions containing only the desired product are combined and concentrated to dryness under reduced pressure (2.7 kPa) at 40° C. After recrystallisation in ethyl acetate, tert-butyl 2-{N-(2-anilinophenyl)-2-[3-(3-methylphenyl)ureido] acetamido}acetate (1.15 g), m.p. 180° C., is obtained.

tert-Butyl 2-[2-amino-N-(2-anilinophenyl)acetamido] acetate may be prepared in the following manner: hydrazine hydrate (1.3 g) is added to a solution of tert-butyl 2-[N-(2-anilinophenyl)-2-phthalimidoacetamido] acetate (4.2 g) in methanol (100 cc). The reaction mixture is stirred for 5 hours at a temperature in the region of 20° C. and then concentrated to dryness under reduced pressure (2.7 kPa) at 40° C. The residue is treated with diethyl ether (200 cc) and the insoluble product is separated by filtration. The filtrate is concentrated to dryness under reduced pressure (2.7 kPa) at 40° C. tert-Butyl 2-[2-amino-N-(2-anilinophenyl)acetamido]acetate (2.6 g) is thereby obtained in the form of an oil, which is used without further purification in the subsequent syntheses.

tert-Butyl 2-[N-(2-anilinophenyl)-2-phthalimidoacetamido] acetate may be prepared in the following manner: an oily suspension (50% by weight) (1.1 g) of sodium hydride is added at a temperature in the region of 10° C. to a solution, maintained under an argon atmosphere, of N-(2-anilinophenyl)-2-phthalimidoacetamide (8.7 g) in anhydrous tetrahydrofuran (100 cc), and the suspension obtained is stirred for 1 hour at a temperature in the region of 20° C. A solution of tert-butyl bromoacetate (4.6 g) in anhydrous tetrahydrofuran (20 cc) is then added and stirring is continued for 3 hours at a temperature in the region of 20° C. The reaction mixture is then poured into a mixture, cooled to a temperature in the region of 0° C., of water (100 cc) and ethyl acetate (200 cc). The aqueous phase is separated after settling has taken place and re-extracted with ethyl acetate (2×20 cc). The organic phases are combined, washed with water (3×25 cc), dried over magnesium sulphate, filtered and then concentrated to dryness under reduced pressure (2.7 kPa) at 40° C. tert-Butyl 2-[N-(2-anilinophenyl)-2-phthalimidoacetamido] acetate (4.2 g), m.p. 205° C., is thereby obtained.

N-(2-Anilinophenyl)-2-phthalimidoacetamide may be prepared in the following manner: a solution of 2-phthalimidoacetyl chloride (11.2 g) in dichloromethane (60 cc) is added, while the temperature is maintained in the region of 20° C., to a solution, maintained under an argon atmosphere, of N-phenyl-1,2-diaminobenzene (9.2 g) and triethylamine (5.1 g) in dichloromethane (60 cc). The solution obtained is stirred for 2 hours at a temperature in the region of 20° C. and then treated with water (100 cc). The aqueous phase is separated after settling has taken place and then re-extracted with dichloromethane (2×50 cc). The organic phases are combined, washed with water (2×30 cc), dried over magnesium sulphate, filtered and then concentrated to dryness under reduced pressure (2.7 kPa) at 40° C. After recrystallisation in ethyl acetate, N-(2-anilinophenyl)-2-phthalimidoacetamide (8.8 g), m.p. 191° C. is thereby obtained

EXAMPLE 31

2-[N-(3-Methoxyphenyl)isocyanatoacetamido]-N-methyl-N-phenylacetamide (3 g) is added at a temperature in the region of 20° C. to a solution, maintained under an argon atmosphere, of 3-(1-hydroxyethyl)aniline (1.1 g) in anhydrous tetrahydrofuran (20 cc). The solution obtained is stirred for 16 hours at a temperature in the region of 20° C. and then concentrated to dryness under reduced pressure (2.7 kPa) at 40° C. The residual oil is purified by chromatography on silica (0.063–0.2 mm) (150 g) contained in a column 2.5 cm in diameter [eluent: dichloromethane/methanol (98:2 by volume)], collecting 20-cc fractions. The fractions containing only the desired product are combined and concentrated to dryness under reduced pressure (2.7 kPa) at 40° C. After recrystallisation in diisopropyl ether, (RS)-2-[2-{3-[3-(1 -hydroxyethyl)phenyl]ureido}-N-(3-methoxyphenyl)acetamido] -N-methyl-N-phenylacetamide (1.7 g), m.p. 115° C., is thereby obtained.

EXAMPLE 32

Using a procedure similar to that described in Example 31, but starting with 3-(1-hydroxyethyl)aniline (0.86 g) and 2-[N-(2-ethoxycarbonylphenyl)isocyanatoacetamido]-N-methyl-N-phenylacetamide (2.8 g), and after recrystallisation in ethyl acetate, 2-[2-{3-[3-(1-hydroxyethyl)phenyl] ureido}-N-(2-ethoxycarbonylphenyl)acetamido] -N-methyl-N-phenyl acetamide (2 g), m.p. 195° C., is obtained.

2-[N-(2-Ethoxycarbonylphenyl)isocyanatoacetamido] -N-methyl-N-phenylacetamide may be prepared in a manner similar to that described in Example 26 for the preparation of 2-[N-(3-methoxyphenyl)isocyanatoacetamido] -N-methyl-N-phenylacetamide, but starting with isocyanatoacetyl chloride (1.1 g), 2-[(2-ethoxycarbonylphenyl)amino] -N-methyl-N-phenylacetamide (2.2 g) and pyridine (0.65 g). 2-[N-(2-Ethoxycarbonylphenyl)isocyanatoacetamido] -N-methyl-N-phenylacetamide (2.8 g) is thereby obtained in the form of an oil, which is used without further purification in the subsequent syntheses.

2-[(2-Ethoxycarbonylphenyl)amino]-N-methyl-N-phenylacetamide may be prepared in a manner similar to that described in Example 26 for the preparation of 2-[(3-methoxyphenyl)amino]-N-methyl-N-phenylacetamide, but starting with 2-[N-(2-ethoxycarbonylphenyl)trifluoroacetamido] -N-methyl-N-phenylacetamide (3.1 g) and 2N aqueous sodium hydroxide solution (7.5 cc). 2-[(2-Ethoxycarbonylphenyl)amino]-N-methyl-N-phenylacetamide (2.2 g), m.p. 100° C., is thereby obtained.

2-[N-(2-Ethoxycarbonylphenyl)trifluoroacetamido] -N-methyl-N-phenylacetamide may be prepared in a manner similar to that described in Example 26 for the preparation of 2-[N-(3-methoxyphenyl)trifluoroacetamido] -N-methyl-N-phenylacetamide, but starting with ethyl 2-(trifluoroacetylamino)benzoate (5.8 g), an oily suspension (50% by weight) (1.3 g) of sodium hydride and 2-bromo-N-methyl-N-phenylacetamide (7.3 g). 2-[N-(2-Ethoxycarbonylphenyl)trifluoroacetamido]-N-methyl-N-phenylacetamide (5.7 g), m.p. 95° C., is thereby obtained.

Ethyl 2-(trifluoroacetylamino)benzoate may be prepared in a manner similar to that described in Example 26 for the preparation of N-(3-methoxyphenyl)trifluoroacetamide, but starting with ethyl 2-aminobenzoate (4.1 g) and trifluoroacetic anhydride (5.3 g). Ethyl 2-(trifluoroacetylamino)benzoate (6.4 g), m.p. 78° C., is thereby obtained.

EXAMPLE 33

Using a procedure similar to that described in Example 31, but starting with 3-(hydroxymethyl)aniline (0.86 g) and 2-[N-(2-ethoxycarbonylphenyl)isocyanatoacetamido]

-N-methyl-N-phenylacetamide (2.9 g), and after recrystallisation in ethyl acetate, 2-[N-(2-ethoxycarbonylphenyl)-2-{3-[3-(hydroxymethyl)phenyl] ureido}acetamido]-N-methyl-N-phenylacetamide (2 g), m.p. 184° C., is obtained.

EXAMPLE 34

Using a procedure similar to that described in Example 31, but starting with 3-(hydroxymethyl)aniline (1.1 g) and 2-[N-(3-methoxyphenyl)isocyanatoacetamido] -N-methyl-N-phenylacetamide (3.2 g), and after recrystallisation in ethyl acetate, 2-[2-{3-[3-(hydroxymethyl)phenyl] ureido}-N-(3-methoxyphenyl)acetamido] -N-methyl-N-phenylacetamide (2.6 g), m.p. 142° C., is obtained.

EXAMPLE 35

Using a procedure similar to that described in Example 27, but starting with 2-[2-amino-N-(3-ethoxycarbonylphenyl)acetamido] -N-methyl-N-phenylacetamide (3.1 g) and 3-methylphenyl isocyanate (1.2 g), and after recrystallisation in diisopropyl ether, 2-{N-(3-ethoxycarbonylphenyl)-2-[3-(3-methylphenyl)ureido] acetammido}-N-methyl-N-phenylacetamide (2 g), m.p. 88° C., is obtained.

2-[2-Amino-N-(3-ethoxycarbonylphenyl)acetamido] -N-methyl-N-phenylacetamide may be prepared in a manner similar to that described in Example 27 for the preparation of tert-butyl 2-{2-amino-N-[2-(3,3-dimethylpiperidino)carbonylphenyl] acetamido}acetate, but starting with 2-[N-(3-ethoxycarbonylphenyl)-2-phthalimidoacetamido] -N-methyl-N-phenylacetamide (4.2 g) and hydrazine hydrate (1.25 g). 2-[2-Amino-N-(3-ethoxycarbonylphenyl)acetamido] -N-methyl-N-phenylacetamide (3 g) is thereby obtained in the form of an oil, which is used without further purification in the subsequent syntheses.

2-[N-(3-Ethoxycarbonylphenyl)-2-phthalimidoacetamido] -N-methyl-N-phenylacetamide may be prepared in a manner similar to that described in Example 27 for the preparation of tert-butyl 2-{N-[2-(3,3-dimethylpiperidino)carbonylphenyl] -2-phthalimidoacetamido}acetate, but starting with N-(3-ethoxycarbonylphenyl)-2-phthalimidoacetamide (3.9 g), an oily suspension (50% by weight) (0.64 g) of sodium hydride and 2-bromo-N-methyl-N-phenylacetamide (3.3 g). 2-[N-(3-Ethoxycarbonylphenyl)-2-phthalimidoacetamido] -N-methyl-N-phenylacetamide (4.2 g) is thereby obtained.

N-(3-Ethoxycarbonylphenyl)-2-phthalimidoacetamide may be prepared in a manner similar to that described in Example 27 for the preparation of N-[2-(3,3-dimethylpiperidino)carbonylphenyl]-2-phthalimidoacetamide, but starting with ethyl 3-aminobenzoate (5 g), triethylamine (3.9 g) and 2-phthalimidoacetyl chloride (8.1 g). After recrystallisation in ethyl acetate, N-(3-ethoxycarbonylphenyl)-2-phthalimidoacetamide (8.7 g), m.p. 215° C., is thereby obtained.

EXAMPLE 36

The procedure used is similar to that described in Example 26, but starting with ethyl 3-{N-(N-methyl-N-phenylcarbamoylmethyl)-2-[3-(3-methylphenyl)ureido] acetamido}benzoate (0.5 g) and 1N aqueous sodium hydroxide solution (1 cc). 3-{N-(N-Methyl-N-phenylcarbamoylmethyl)-2 -[3-(3-methylphenyl)ureido] acetamido}benzoic acid (0.3 g), m.p. 140° C., is thereby obtained.

EXAMPLE 37

The procedure used is similar to that described in Example 26, but starting with ethyl 3-{3-[N-(3-methoxyphenyl)-N-(N-methyl-N-phenylcarbamoylmethyl)carbamoylmethyl] ureido}phenylacetate (2.45 g) and 1N aqueous sodium hydroxide solution (4.6 cc). 3-{3-[N-(3-Methoxyphenyl)-N-(N-methyl-N-phenylcarbamoylmethyl)carbamoylmethyl] ureido}phenylacetic acid (1.6 g), m.p. 120° C., is thereby obtained.

Ethyl 3-{3-[N-(3-methoxyphenyl)-N-(N-methyl-N-phenylcarbamoylmethyl)carbamoylmethyl] ureido}phenylacetate may be prepared in a manner similar to that described in Example 26 for the preparation of ethyl 3-{3-[N-(3-methoxyphenyl)-N-(N-methyl-N-phenylcarbamoylmethyl)carbamoylmethyl] ureido}benzoate, but starting with 2-[N-(3-methoxyphenyl)isocyanatoacetamido] -N-methyl-N-phenylacetamide (2.4 g) and ethyl 3-aminophenylacetate (1.1 g). The crude product is purified by chromatography on silica (0.063–0.2 mm) (60 g) contained in a column 2.0 cm in diameter [eluent: dichloromethane/ethyl acetate (20:80 by volume)], collecting 20-cc fractions. Fractions 8 to 18 are combined and concentrated to dryness under reduced pressure (2.7 kPa) at 40° C. Ethyl 3-{3-[N-(3 -methoxy-phenyl)-N-(N-methyl-N-phenylcarbamoylmethyl)carbamoylmethyl] ureido}phenylacetate (2.45 g) is thereby obtained in the form of an amorphous powder, which is used without further purification in the subsequent syntheses.

Ethyl 3-aminophenylacetate may be prepared in the following manner: palladium on charcoal (5% Pd) (0.1 g) is added to a solution of ethyl 3-nitrophenylacetate (2.0 g) in ethanol (20 cc). The suspension is stirred for 2 hours at a temperature in the region of 25° C. under a hydrogen atmosphere (100 kPa). The catalyst is separated by filtration and the filtrate is concentrated to dryness under reduced pressure (2.7 kPa) at 40° C. Ethyl 3-aminophenylacetate (1.7 g) is thereby obtained in the form of an oil, which is used without further purification in the subsequent syntheses.

Ethyl 3-nitrophenylacetate may be prepared according to the method described by SEGERS and A. BRUYLANTS, Bul. Soc. Chim. Belg., 64, 87 (1955).

EXAMPLE 38

A suspension of 3-{3-[N-(3-methoxyphenyl)-N-(N-methyl-N-phenylcarbamoylmethyl)carbamoylmethyl] ureido} phenylacetic acid (0.8 g) in dichloromethane (15 cc) is added in the course of 5 minutes to a solution, maintained under a nitrogen atmosphere at a temperature in the region of −55° C. of boron tribromide (1.2 g) in dichloromethane (20 cc). The mixture obtained is stirred for 15 minutes at a temperature in the region of −55° C., and then 20 hours at a temperature in the region of 20° C. Water (20 cc) and then 1N aqueous sodium hydroxide solution (5 cc) are then added. The organic phase is separated after settling has taken place and the aqueous phase is washed with ethyl acetate (2×20 cc) and then acidified with 1N aqueous hydrochloric acid solution (5 cc). The precipitate formed is separated by filtration, washed with water (3×5 cc) and dried in the air. 3-{3-[N-(3 -Hydroxyphenyl)-N-(N-methyl-N-phenylcarbamoylmethyl)carbamoylmethyl] ureido}phenylacetic acid (0.3 g), m.p. 148° C. is thereby obtained

EXAMPLE 39

Using a procedure similar to that described in Example 1, but starting with 2-[2-amino-N-(2-methylphenyl)acetamido]

-N-methyl-N-phenylacetamide (1.2 g) and 3-methylphenyl isocyanate (1.3 g), and after recrystallisation in ethyl acetate, 2-{N-(2-methyl-phenyl)-2 -[3-(3-methylphenyl)ureido]acetamido}-N-methyl-N-phenylacetamide (2.3 g), m.p. 193° C., is obtained.

2-[2-Amino-N-(2-methylphenyl)acetamido]-N-methyl-N-phenylacetamide may be prepared in a manner similar to that in Example 4 for the preparation of tert-butyl 2-[2-amino-N-(2-trifluoromethoxyphenyl)acetamido] acetate, but starting with 2-[N-(2-methylphenyl)-2 -phthalimidoacetamido]-N-methyl-N-phenylacetamide (5.3 g) and hydrazine hydrate (1.2 g). 2-[2-Amino-N-(2-methylphenyl)acetamido]-N-methyl-N-phenylacetamide (3.8 g) is thereby obtained in the form of an oil, which is used without further purification in the subsequent syntheses.

2-[N-(2-Methylphenyl)-2-phthalimidoacetamido] -N-methyl-N-phenylacetamide may be prepared in a manner similar to that described in Example 4 for the preparation of tert-butyl-2-[2-phthalimido-N-(2-trifluoromethoxyphenyl)acetamido] acetate, but starting with N-(2-methylphenyl)-2-phthalimidoacetamide (5.9 g), an oily suspension (50% by weight) (1.15 g) of sodium hydride and 2-bromo-N-methyl-N-phenylacetamide (6.8 g). After recrystallisation in isopropyl ether, 2-[N-(2-methylphenyl)-2-phthalimidoacetamido]-N-methyl-N-phenylacetamide (7.1 g), m.p. 120° C., is thereby obtained.

N-(2-methylphenyl)-2-phthalimidoacetamide may be prepared in a manner similar to that described in Example 4 for the preparation of 2-phthalimido-N-(2-trifluoromethoxyphenyl)acetamide, but starting with 2-methylaniline (5.4 g), triethylamine (6.6 g) and 2-phthalimidoacetyl chloride (13.4 g). After recrystallisation in ethyl acetate, N-(2-methylphenyl)-2-phthalimidoacetamide (14.4 g), m.p. 254° C., is thereby obtained.

EXAMPLE 40

Using a procedure similar to that described in Example 1, but starting with 2-[2-amino-N-(2-methoxyphenyl)acetamido] -N-methyl-N-phenylacetamide (2.0 g) and 3-methylphenyl isocyanate (0.64 g), and after recrystallisation in ethyl acetate, 2-{N-(2-methoxyphenyl)-2 -[3-(3-methylphenyl)ureido]acetamido}-N-methyl-N-phenylacetamide (1.5 g), m.p. 212° C., is obtained.

2-[2-Amino-N-(2-methoxyphenyl)acetamido]-N-methyl-N-phenylacetamide may be prepared in a manner similar to that described in Example 4 for the preparation of tert-butyl 2-[2-amino-N-(2-trifluoromethoxyphenyl)acetamido] acetate, but starting with 2-[N-(2-methoxyphenyl)-2-phthalimidoacetamido]-N-methyl-N-phenylacetamide (4.0 g) and hydrazine hydrate (1.3 g). 2-[2-Amino-N-(2-methoxyphenyl)acetamido]-N-methyl-N-phenylacetamide (2.0 g) is thereby obtained in the form of an oil, which is used without further purification in the subsequent syntheses.

2-[N-(2-Methoxyphenyl)-2-phthalimidoacetamido] -N-methyl-N-phenylacetamide may be prepared in a manner similar to that described in Example 4 for the preparation of tert-butyl 2-[2-phthalimido-N-(2-trifluoromethoxyphenyl)acetamido] acetate, but starting with N-(2-methoxyphenyl)-2-phthalimidoacetamide (6.2 g), an oily suspension (50% by weight) (1.15 g) of sodium hydride and 2-bromo-N-methyl-N-phenylacetamide (6.8 g). After recrystallisation in ethyl acetate, 2-[N-(2-methoxyphenyl)-2-phthalimidoacetamido] -N-methyl-N-phenylacetamide (5.1 g), m.p. 199° C., is thereby obtained.

N-(2-Methoxyphenyl)-2-phthalimidoacetamide may be prepared in a manner similar to that described in Example 4 for the preparation of 2-phthalimido-N-(2-trifluoromethoxyphenyl)acetamide, but starting with 2-methoxyaniline (6.7 g), triethylamine (6.6 g) and 2-phthalimidoacetyl chloride (13.4 g). After recrystallisation in acetonitrile, N-(2-methoxyphenyl)-2-phthalimidoacetamide (14.6 g), m.p. 211° C., is thereby obtained.

EXAMPLE 41

Using a procedure similar to that described in Example 1, but starting with tert-butyl 2-[2-amino-N-(2 -phenoxyphenyl)acetamido]acetate (4.7 g) and 3-methylphenyl isocyanate (1.9 g), and after recrystallisation in ethyl acetate, tert-butyl 2-{2-[3-(3-methylphenyl)ureido]-N-(2-phenoxyphenyl)acetamido} acetate (1.7 g), m.p. 204° C., is obtained.

tert-Butyl 2-[2-amino-N-(2-phenoxyphenyl)acetamido] acetate may be prepared in a manner similar to that described in Example 4 for the preparation of tert-butyl 2-[2-amino-N-(2-trifluoromethoxyphenyl)acetamido] acetate, but starting with tert-butyl 2-[N-(2-phenoxyphenyl)-2 -phthalimidoacetamido]acetate (6.3 g) and hydrazine hydrate (2 g). tert-Butyl 2-[2-amino-N-(2-phenoxyphenyl)acetamido]acetate (4.7 g) is thereby obtained in the form of an oil, which is used without further purification in the subsequent syntheses.

tert-Butyl 2-[N-(2-phenoxyphenyl)-2-phthalimidoacetamido] acetate may be prepared in a manner similar to that described in Example 4 for the preparation of tert-butyl 2-[2-phthalimido-N-(2-trifluoromethoxyphenyl)acetamido] acetate, but starting with N-(2-phenoxyphenyl)-2-phthalimidoacetamide (7.5 g), an oily suspension (50% by weight) (1.1 g) of sodium hydride and tert-butyl bromoacetate (4.3 g). tert-Butyl 2-[N-(2-phenoxyphenyl)-2-phthalimidoacetamido] acetate (7.1 g), m.p. 145° C., is thereby obtained.

N-(2-phenoxyphenyl)-2-phthalimidoacetamide may be prepared in a manner similar to that described in Example 4 for the preparation of 2-phthalimido-N-(2-trifluoromethoxyphenyl)acetamide, but starting with 2-phenoxyaniline (4.6 g), triethylamine (2.5 g) and 2-phthalimidoacetyl chloride (5.6 g). N-(2-Phenoxyphenyl)-2 -phthalimidoacetamide (8.3 g), m.p. 143° C., is thereby obtained.

EXAMPLE 42

Using a procedure similar to that described in Example 1, but starting with tert-butyl 2-[2-amino-N-(2-biphenylyl)acetamido] acetate (5.8 g) and 3-methylphenyl isocyanate (2.3 g), and after recrystallisation in ethyl acetate, tert-butyl 2-{N-(2-biphenylyl)-2-[3-(3-methylphenyl)ureido] acetamido}acetate (3.7 g), m.p. 177° C., is obtained.

tert-Butyl 2-[2-amino-N-(2-biphenylyl)acetamido] acetate may be prepared in a manner similar to that described in Example 4 for the preparation of tert-butyl 2-[2-amino-N-(2-trifluoromethoxyphenyl)acetamido] acetate, but starting with tert-butyl 2-[N-(2-biphenylyl)-2-phthalimidoacetamido]acetate (7.5 g) and hydrazine hydrate (2.4 g). tert-Butyl 2-[2-amino-N-(2-biphenylyl)acetamido] acetate (5.8 g) is thereby obtained in the form of an oil, which is used without further purification in the subsequent syntheses.

tert-Butyl 2-[N-(2-biphenylyl)-2-phthalimidoacetamido] acetate may be prepared in a manner similar to that described in Example 4 for the preparation of tert-butyl 2-[2-phthalimido-N-(2-trifluoromethoxyphenyl)acetamido] acetate, but starting with N-(2-biphenylyl)-2-phthalimidoacetamide (6.5 g), an oily suspension (50% by weight) (0.87 g) of sodium hydride and tert-butyl bromoacetate (3.6 g). tert-Butyl 2-[N-(2-biphenylyl)-2-phthalimidoacetamido]acetate (8 g), m.p. 145° C., is thereby obtained.

N-(2-Biphenylyl)-2-phthalimidoacetamide may be prepared in a manner similar to that described in Example 4 for the preparation of 2-phthalimido-N-(2-trifluoromethoxyphenyl)acetamide, but starting with 2-aminobiphenyl (4.2 g), triethylamine (2.7 g) and 2-phthalimidoacetyl chloride (5.6 g). 2-Phthalimido-N-(2-biphenylyl)acetamide (7.1 g), m.p. 204° C., is thereby obtained.

EXAMPLE 43

Using a procedure similar to that described in Example 1, but starting with tert-butyl 2-[2-amino-N-(2-benzylphenyl)acetamido] acetate (8.1 g) and 3-methylphenyl isocyanate (3 g), and after recrystallisation in ethyl acetate, tert-butyl 2-{N-(2-benzylphenyl)-2-[3-(3-methylphenyl)ureido]acetamido} acetate (6.6 g), m.p 183° C., is obtained tert-Butyl 2-[2-amino-N-(2-benzylphenyl)acetamido] acetate may be prepared in a manner similar to that described in Example 4 for the preparation of tert-butyl 2-[2-amino-N-(2-trifluoromethoxyphenyl)acetamido] acetate, but starting with tert-butyl 2-[N-(2-benzylphenyl)-2-phthalimidoacetamido]acetate (11.2 g) and hydrazine hydrate (3.5 g). tert-Butyl 2-[2-amino-N-(2-benzylphenyl)acetamido]acetate (8.1 g) is thereby obtained in the form of an oil, which is used without further purification in the subsequent syntheses.

tert-Butyl 2-[N-(2-benzylphenyl)-2phthalimidoacetamido] acetate may be prepared in a manner similar to that described in Example 4 for the preparation of tert-butyl 2-[2-phthalimido-N-(2-trifluoromethoxyphenyl)acetamido] acetate, but starting with N-(2-benzylphenyl)-2-phthalimidoacetamide (9.3 g), an oily suspension (50% by weight) (1.4 g) of sodium hydride and tert-butyl bromoacetate (5.9 g). tert-Butyl 2-[N-(2-benzylphenyl)-2-phthalimidoacetamido]acetate (11.3 g), m.p. 190° C. is thereby obtained N-(2-Benzylphenyl)-2-phthalimidoacetamide may be prepared in a manner similar to that described in Example 4 for the preparation of 2-phthalimido-N-(2-trifluoromethoxyphenyl)acetamide, but starting with 2-benzylaniline (4.6 g), triethylamine (3 g) and 2-phthalimidoacetyl chloride (7.3 g). N-(2-Benzylphenyl)-2-phthalimidoacetamide (9.3 g), m.p. 232° C., is thereby obtained.

EXAMPLE 44

Using a procedure similar to that described in Example 1, but starting with tert-butyl 2-[2-amino-N-(3-ethoxycarbonylphenyl)acetamido] acetate (3.3 g) and 3-methylphenyl isocyanate (1.3 g), and after recrystallisation in diisopropyl ether, tert-butyl 2-{N-(3-ethoxycarbonylphenyl)-2-[3-(3-methylphenyl)ureido] acetamido}acetate (0.85 g), m.p. 71° C., is obtained.

tert-Butyl 2-[2-amino-N-(3-ethoxycarbonylphenyl)acetamido] acetate may be prepared in a manner similar to that described in Example 4 for the preparation of tert-butyl 2-[2-amino-N-(2-trifluoromethoxyphenyl)acetamido] acetate, but starting with tert-butyl 2-[N-(3-ethoxycarbonylphenyl)-2-phthalimidoacetamido] acetate (5 g) and hydrazine hydrate (1.6 g). tert-Butyl 2-[2-amino-N-(3-ethoxycarbonylphenyl)acetamido] acetate (3.3 g) is thereby obtained in the form of an oil, which is used without further purification in the subsequent syntheses.

tert-Butyl 2-[N-(3-ethoxycarbonylphenyl)-2-phthalimidoacetamido] acetate may be prepared in a manner similar to that described in Example 4 for the preparation of tert-butyl 2-[2-phthalimido-N-(2-trifluoromethoxyphenyl)acetamido] acetate, but starting with N-(3-ethoxycarbonylphenyl)-2-phthalimidoacetamide (6 g), an oily suspension (50% by weight) (1 g) of sodium hydride and tert-butyl bromoacetate (4 g). tert-Butyl 2-[N-(3-ethoxycarbonylphenyl)-2-phthalimidoacetamido] acetate (5.1 g) is thereby obtained in the form of an oil, which is used without further purification in the subsequent syntheses.

N-(3-Ethoxycarbonylphenyl)-2-phthalimidoacetamide may be prepared in a manner similar to that described in Example 4 for the preparation of 2-phthalimido-N-(2-trifluoromethoxyphenyl)acetamide, but starting with ethyl 3-aminobenzoate (3.3 g), triethylamine (2.4 g) and 2-phthalimidoacetyl chloride (5.8 g). N-(3-ethoxycarbonylphenyl)-2-phthalimidoacetamide (6.2 g), m.p. 219° C., is thereby obtained.

EXAMPLE 45

Using a procedure similar to that described in Example 1, but starting with 2-[2-amino-N-(2-ethoxycarbonylphenyl)acetamido] -N-methyl-N-phenylacetamide (2.25 g) and 3-methylphenyl isocyanate (0.88 g), and after recrystallisation in ethyl acetate, 2-{N-(2-ethoxycarbonylphenyl)-2-[3-(3-methylphenyl)ureido] acetamido}-N-methyl-N-phenylacetamide (1.6 g), m.p. 201° C., is obtained.

2-[2-Amino-N-(2-ethoxycarbonylphenyl)acetamido] -N-methyl-N-phenylacetamide may be prepared in a manner similar to that described in Example 4 for the preparation of tert-butyl 2-[2-amino-N-(2-trifluoromethoxyphenyl)acetamido] acetate, but starting with 2-[N-(2-ethoxycarbonylphenyl)-2-phthalimidoacetamido] -N-methyl-N-phenylacetamide (3.0 g) and hydrazine hydrate (0.9 g). 2-[2-Amino-N-(2-ethoxycarbonylphenyl)acetamido] -N-methyl-N-phenylacetamide (2.25 g) is thereby obtained in the form of an oil, which is used without further purification in the subsequent syntheses.

2-[N-(2-Ethoxycarbonylphenyl)-2-phthalimidoacetamido] -N-methyl-N-phenylacetamide may be prepared in a manner similar to that described in Example 4 for the preparation of tert-butyl 2-[2-phthalimido-N-(2-trifluoromethoxyphenyl)acetamido] acetate, but starting with N-(2-ethoxycarbonylphenyl)-2-phthalimidoacetamide (5.4 g), an oily suspension (50% by weight) (0.9 g) of sodium hydride and 2-bromo-N-methyl-N-phenylacetamide (5.25 g). After recrystallisation in ethyl acetate, 2-[N-(2-ethoxycarbonylphenyl)-2-phthalimidoacetamido]-N-methyl-N-phenylacetamide (3.0 g), m.p. 202° C., is thereby obtained.

N-(2-Ethoxycarbonylphenyl)-2-phthalimidoacetamide may be prepared in a manner similar to that described in Example 4 for the preparation of 2-phthalimido-N-(2-trifluoromethoxyphenyl)acetamide, but starting with ethyl 2-aminobenzoate (4.1 g), triethylamine (2.8 g) and 2-phthalimidoacetyl chloride (5.6 g). After recrystallisation in ethyl acetate, N-(2-ethoxycarbonylphenyl)-2-phthalimidoacetamide (8.7 g), m.p. 197° C., is thereby obtained.

EXAMPLE 46

Using a procedure similar to that described in Example 27, but starting with 2-{2-amino-N-[2-(N-methylanilino)carbonylphenyl] acetamido}-N-methyl-N-phenylacetamide (2 g) and 3-methylphenyl isocyanate (0.62 g), 2-{N-[2-(N-methylanilino)carbonylphenyl]-2-[ 3-(3- methylphenyl)ureido]acetamido}-N-methyl-N-phenylacetamide (1.45 g), m.p. 140° C., is obtained.

2-{2-Amino-N-[2-(N-methylanilino)carbonylphenyl]acetamido}-N-methyl-N-phenylacetamide may be prepared in a manner similar to that described in Example 27 for the preparation of tert-butyl 2-{2-amino-N-[2-(3,3-dimethylpiperidino)carbonylphenyl] acetamido}acetate, but starting with N-methyl-2-{ N-[2-(N-methylanilino)carbonylphenyl] -2-phthalimidoacetamido} -N-phenylacetamide (2.8 g) and hydrazine hydrate (0.75 g). 2-{2-Amino-N-[2-(N-methylanilino)carbonylphenyl] acetamido}-N-methyl-N-phenylacetamide (2 g) is thereby obtained in the form of an oil, which is used without further purification in the subsequent syntheses.

N-Methyl-2-{N-[2-(N-methylanilino)carbonylphenyl] -2-phthalimidoacetamido]-N-phenylacetamide may be prepared in the following manner: a solution of 2-bromo-N-methyl-N-phenylacetamide (4.6 g) in N,N-dimethylformamide (25 cc) is added at a temperature in the region of 20° C. to a suspension of N-[2-(N-methylanilino)carbonylphenyl] -2-phthalimidoacetamide (8.3 g) and potassium carbonate (3 g) in N,N-dimethylformamide (50 cc). The mixture obtained is stirred for 120 hours at a temperature in the region of 20° C. and then poured into water (800 cc). The insoluble product is separated by filtration, washed with water (4×100 cc), dried in the air and purified by chromatography on silica (0.04–0.063 mm) (90 g) contained in a column 3.2 cm in diameter (eluent: dichloromethane), collecting 50-cc fractions. Fractions 60 to 90 are combined and concentrated to dryness under reduced pressure (2.7 kPa) at 50° C. N-Methyl-2-{N-[2-(N-methylanilino)carbonylphenyl] -2-phthalimidoacetamido} -N-phenylacetamide (2.8 g) is thereby obtained in the form of an amorphous solid, which is used without further purification in the subsequent syntheses.

EXAMPLE 47

Using a procedure similar to that described in Example 27, but starting with 2-amino-N-(3,3- dimethylpiperidinocarbonylmethyl)-N-[ 2-(N-methylanilino)carbonylphenyl] acetamide (1.45 g) and ethyl 3-isocyanatobenzoate (0.63 g), ethyl 3-[3-{N-(3,3-dimethylpiperidinocarbonylmethyl)-N-[ 2-(N-methylanilino)carbonylphenyl] carbamoylmethyl}ureido]benzoate (1 g), m.p. 225° C., is obtained.

2-Amino-N-(3,3-dimethylpiperidinocarbonyl-methyl)-N-[ 2-(N-methylanilino)carbonylphenyl]acetamide may be prepared in a manner similar to that described in Example 27 for the preparation of tert-butyl 2-{2-amino-N-[2-(3,3-dimethylpiperidino)carbonylphenyl] acetamido}acetate, but starting with N-(3,3-dimethylpiperidinocarbonylmethyl)-N-[ 2-(N-methylanilino)carbonylphenyl] -2-phthalimidoacetamide (2.3 g) and hydrazine hydrate (0.6 g). 2-Amino-N-(3,3-dimethylpiperidinocarbonylmethyl)-N-[ 2-(N-methylanilino)carbonylphenyl] acetamide (1.45 g) is thereby obtained in the form of an oil, which is used without further purification in the subsequent syntheses.

N-(3,3-Dimethylpiperidinocarbonylmethyl)-N-[ 2-(N-methylanilino)carbonylphenyl]-2-phthalimidoacetamide may be prepared in the following manner: N,N'-carbonyldiimidazole (2.35 g) and 3,3-dimethylpiperidine (1.6 g) are added successively at a temperature in the region of 20° C. to a solution of 2-{N-[2-(N-methylanilino)carbonylphenyl] -2-phthalimidoacetamido} acetic acid (6.8 g) and 4-(N,N-dimethylamino)pyridine (30 mg) in tetrahydrofuran (150 cc). The mixture is stirred for 70 hours at a temperature in the region of 20° C. and then concentrated to dryness under reduced pressure (2.7 kPa) at 50° C. The residue is dissolved in dichloromethane (250 cc) and the solution thereby obtained is washed with normal aqueous sodium hydroxide solution (2×75 cc) and then with water (100 cc). The organic phase is dried over magnesium sulphate, filtered and concentrated to dryness under reduced pressure (2.7 kPa) at 60° C. N-(3,3-dimethylpiperidinocarbonylmethyl)-N-[ 2-(N-methylanilino)carbonylphenyl]-2 -phthalimidoacetamide (6.6 g), m.p. 180° C., is thereby obtained.

2-{N-[2-(N-Methylanilino)carbonylphenyl]-2-phthalimidoacetamideo} acetic acid may be prepared in the following manner: a solution of tert-butyl 2-{N-[2-(N-methylanilino)carbonylphenyl] -2-phthalimidoacetamido] acetate (7.9 g) in trifluoroacetic acid (30 cc) is stirred at a temperature in the region of 20° C. for 24 hours and then poured into water (50 cc). The aqueous phase is extracted with dichloromethane (3×250 cc). The organic phases are combined, washed with water (2×150 cc), dried over magnesium sulphate, filtered and then concentrated to dryness under reduced pressure (2.7 kPa) at 60° C. The residue is treated with petroleum ether (100 cc) and the insoluble product is separated by filtration and dried under reduced pressure (15 kPa) at 30° C. 2-{N-[2-(N-Methylanilino)carbonylphenyl] -2-phthalimidoacetamido}acetic acid (6.8 g) is thereby obtained in the form of an amorphous solid, which is used without further treatment in the subsequent syntheses.

EXAMPLE 48

Using a procedure similar to that described in Example 27, but starting with tert-butyl 2-[2-amino-N-(2 -tert-butoxycarbonylphenyl)acetamido]acetate (1.8 g) and 3-methylphenyl isocyanate (0.64 g), tert-butyl 2-{2-[3-(3-methylphenyl)ureido]-N-(2-tert-butoxycarbonylphenyl)acetamido} acetate (1.3 g), m.p. 146° C., is obtained.

tert-Butyl 2-[2-amino-N-(2-tert-butoxycarbonylphenyl)acetamido] acetate may be prepared in a manner similar to that described in Example 27 for the preparation of tert-butyl 2-{2-amino-N-[2-(3,3-dimethylpiperidino)carbonylphenyl] acetamido}acetate, but starting with tert-butyl 2-[2-phthalimido-N-(2-tert-butoxycarbonylphenyl)acetamido] acetate (2.4 g) and hydrazine hydrate (0.7 g). tert-Butyl 2-[2-amino-N-(2 -tert-butoxycarbonylphenyl)acetamido]acetate (1.8 g) is thereby obtained in the form of an oil, which is used without further purification in the subsequent syntheses.

tert-Butyl 2-[2-phthalimido-N-(2-tert-butoxycarbonylphenyl)acetamido] acetate may be prepared in a manner similar to that described in Example 46 for the preparation of 2-{N-[2-(N-methylanilino)carbonylphenyl] -2-phthalimidoacetamido}-N-methyl-N-phenylacetamide, but starting with tert-butyl 2-(2-phthalimidoacetamido)benzoate (3.8 g), tert-butyl bromoacetate (2.15 g) and potassium carbonate (1.5 g). tert-Butyl 2-[N-(2-tert-butoxycarbonylphenyl)phthalimido] acetate (2 g), m.p. 143° C., is thereby obtained.

tert-Butyl 2-(2-phthalimidoacetamido)benzoate may be prepared in a manner similar to that described in Example 27 for the preparation of N-[2-(3,3-dimethylpiperidino)carbonylphenyl] -2-phthalimidoacetamide, but starting with tert-butyl anthranilate (3.3 g), 2-phthalimidoacetyl chloride (4.96 g) and triethylamine (2.24 g). tert-Butyl 2-(2-phthalimidoacetamido)benzoate (5.6 g), m.p. 159° C., is thereby obtained.

tert-Butyl anthranilate may be prepared according to the method described by W. E. Gaines and N. B. Carson, J. Econ. Entomol., 39, 763 (1946).

EXAMPLE 49

2-(3-Aminophenyl)ethanol (1.1 g) is added to a solution of 2-{2-[(1-imidazolyl)carboxamido]-N-(3-methoxyphenyl)acetamido} -N-methyl-N-phenylacetamide (1.7 g) in toluene (35 cc). The mixture is heated to reflux for 4 hours and then concentrated to dryness under reduced pressure (2.7 kPa) at 45° C. The residue is dissolved in ethyl acetate (60 cc) and the solution obtained is washed with 2N aqueous hydrochloric acid solution (20 cc) and then with water (2×25 cc). The organic phase is dried over magnesium sulphate and concentrated to dryness under reduced pressure (2.7 kPa) at 40° C. The crude product obtained is purified by chromatography on silica (0.065–0.205 mm) (50 g) contained in a column 2.1 cm in diameter [eluent: ethyl acetate/ethanol (95:5 by volume)], collecting 20 cc fractions. Fractions 4 to 6 are combined and concentrated to dryness under reduced pressure (2.7 kPa) at 40° C. After recrystallisation in a diisopropyl ether/ethyl acetate (90:10 by volume) mixture, 2-[2-{3-[3-(2-hydroxyethyl)phenyl]ureido}-N-(3 -methoxyphenyl)acetamido]-N-methyl-N-phenylacetamide (0.85 g), m.p. 90° C., is obtained.

2-{2-[(1-Imidazolyl)carboxamido]-N-(3 -methoxyphenyl)acetamido}-N-methyl-N-phenylacetamide may be prepared in the following manner: a solution of 2-[2-amino-N-(3-methoxyphenyl)acetamido]-N-methyl-N-phenylacetamide (3.1 g) in anhydrous tetrahydrofuran (30 cc) is added to a solution of N,N'-carbonyldiimidazole (3.0 g) in anhydrous tetrahydrofuran (30 cc). The solution is stirred for 16 hours at a temperature in the region of 25° C. and then concentrated to dryness under reduced pressure (2.7 kPa) at 40° C. The residue is dissolved in ethyl acetate (50 cc) and the solution obtained is washed successively with water (4×30 cc) and with saturated aqueous sodium chloride solution (30 cc). The organic phase is dried over magnesium sulphate and then concentrated to dryness under reduced pressure (2.7 kPa) at 40° C. After recrystallisation in ethyl acetate, 2-{2-[(1-imidazolyl)carboxamido] N-(3-methoxyphenyl)acetamido}-N-methyl-N-phenylacetamide (3.5 g), m.p. 130° C., is obtained.

2-(3-Aminophenyl)ethanol may be prepared according to the method described by B. CARNMALM et al., Acta Pharm. Suedica, 11, 33 (1974).

EXAMPLE 50

The procedure used is similar to that described in Example 26, but starting with methyl (RS)-2-[3-{3-[N-(3-methoxyphenyl)-N-(N-methyl-N-phenylcarbamoylmethyl)carbamoylmethyl] ureido}phenyl]propionate (2 g) and 1N aqueous sodium hydroxide solution (3.8 cc). (RS)-2-[3-{3-[N-(3-Methoxyphenyl)-N-(N-methyl-N -phenylcarbamoylmethyl)carbamoylmethyl] ureido} phenyl]propionic acid (1.3 g), m.p. 127° C., is thereby obtained.

Methyl (RS)-2-[3-{3-[N-(3-methoxyphenyl)-N-(N-methyl-N -phenylcarbamoylmethyl)carbamoylmethyl]ureido} phenyl]propionate may be prepared in a manner similar to that described in Example 49 for the preparation of 2-[2-{3-[3-(2-hydroxyethyl)phenyl]ureido} -N-(3-methoxyphenyl)acetamido]-N-methyl-N-phenylacetamide, but starting with 2-{2-[(1-imidazolyl)carboxamido] -N-(3-methoxyphenyl)acetamido} -N-methyl-N-phenylacetamide (2.5 g) and methyl (RS)-2-(3 -aminophenyl)propionate (2.1 g). The crude product obtained is purified by chromatography on silica (0.065–0.200 mm) (50 g) contained in a column 2.5 cm in diameter [eluent: methylene chloride/ethyl acetate (60:40 by volume)], collecting 50-cc fractions. Fractions 5 to 12 are combined and concentrated to dryness under reduced pressure (2.7 kPa) at 40° C. Methyl (RS)-2-[3-{3-[N-(3-Methoxyphenyl)-N-(N-methyl-N-phenylcarbamoylmethyl)carbamoylmethyl] ureido}phenyl]-propionate (2.1 g) is thereby obtained in the form of a meringue-like product, which is used without further purification in the subsequent syntheses.

Methyl (RS)-2-(3-aminophenyl)propionate may be prepared in the following manner: palladium on charcoal (5% Pd) (0.3 g) is added to a solution of methyl (RS)-2-(3-nitrophenyl)propionate (4 g) in ethanol (50 cc). The suspension is stirred for 2 hours at a temperature in the region of 25° C. under a hydrogen atmosphere (100 kPa). The catalyst is then separated by filtration and the filtrate is concentrated to dryness under reduced pressure (2.7 kPa) at 40° C. Methyl (RS)-2-(3-aminophenyl)propionate (3.3 g) is thereby obtained in the form of an oil, which is used without further purification in the subsequent syntheses.

Methyl (RS)-2-(3-nitrophenyl)propionate may be prepared in the following manner: hydrochloric acid is bubbled for 3 hours into a solution of (RS)-2-(3-nitrophenyl)propionitrile (5 g) in methanol (40 cc). The mixture obtained is stirred under reflux for 30 minutes and the insoluble product is separated by filtration. The filtrate is concentrated to dryness under reduced pressure (2.7 kPa) at 40° C. The crude product is purified by chromatography on silica (0.065–0.200 mm) (80 g) contained in a column 3.5 cm in diameter [eluent: petroleum ether/ethyl acetate (80:20 by volume)], collecting 100-cc fractions. Fractions 1 and 2 are combined and concentrated to dryness under reduced pressure (2.7 kPa) at 40° C. Methyl (RS)-2-(3-nitrophenyl)propionate (4.0 g) is thereby obtained in the form of an oil, which is used without further purification in the subsequent syntheses.

(RS)-2-(3-Nitrophenyl)propionitrile may be prepared according to the method described by E. Felder et al., J. Med. Chem., 13, 559 (1970).

EXAMPLE 51

The procedure used is similar to that described in Example 49, but starting with 2-{2-[ (1-imidazolyl)carboxamido]-N-(3-methoxyphenyl)acetamido} -N-methyl-N-phenylacetamide (1.7 g) and 5-(3-aminobenzyl)tetrazole (1.4 g). The crude product obtained is purified by chromatography on silica (0.065–0.200 mm) (40 g) contained in a column 2 cm in diameter [eluent: methylene chloride/ethanol (90:10 by volume)], collecting 25-cc fractions. Fractions 5 to 123 are combined and concentrated to dryness under reduced pressure (2.7 kPa) at 40° C. After recrystallisation in an ethyl acetate/diisopropyl ether (10:90 by volume) mixture, 2-{N-(3-methoxyphenyl)-2-[3-{ 3-[(5-tetrazolyl)methyl] phenyl}ureido]acetamido}-N-methyl-N-phenylacetamide (0.2 g), m.p. 120° C., is thereby obtained.

5-(3-Aminobenzyl)tetrazole may be prepared in the following manner: palladium on charcoal (5% Pd) (0.3 g) is added to a solution of 5-(3-nitrobenzyl)tetrazole (3.9 g) in ethanol (80 cc). The suspension is stirred for 2 hours at a temperature in the region of 25° C. under a hydrogen atmosphere (100 kPa). The catalyst is separated by filtration and the filtrate is concentrated to dryness under reduced pressure (2.7 kPa) at 40° C. 5-(3-Aminobenzyl)tetrazole (3.1 g), m.p. 140° C. is thereby obtained.

5-(3-Nitrobenzyl)tetrazole may be prepared in the following manner: sodium azide (1.43 g) and anhydrous ammonium chloride (1.17 g) are added to a solution of 3-nitrophenylacetonitrile (1.6 g) in anhydrous dimethylformamide (25 cc). The mixture is stirred at a temperature in the region of 100° C. for 22 hours and then concentrated to dryness under reduced pressure (1.2 kPa) at 80° C. The residue obtained is taken up with 2N hydrochloric acid solution (25 cc) and the mixture obtained is extracted with methylene chloride (2×50 cc). The combined organic phases are dried over magnesium sulphate and concentrated to dryness under reduced pressure (2.7 kPa) at 35° C. 5-(3-Nitrobenzyl)tetrazole (16 g), m.p. 140° C. is thereby obtained.

3-Nitrophenylacetonitrile may be prepared in the following manner [lacuna] 8.5M aqueous potassium cyanide solution (20 cc) is added to a solution of 3-nitro-benzyl chloride (20.6 g) in methanol (120 cc). The mixture is stirred under reflux for 4 hours and then concentrated to dryness under reduced pressure (2.7 kPa) at 45° C. The residue is taken up with diethyl ether (200 cc) and water (150 cc). The organic phase is dried over magnesium sulphate and concentrated to dryness under reduced pressure (2.7 kPa) at 35° C. The crude product obtained is purified by chromatography on silica (0.065–0.200 mm) (50 g) contained in a column 2 cm in diameter (eluent: methylene chloride), collecting 30-cc fractions. Fractions 4 to 9 are combined and concentrated to dryness under reduced pressure (2.7 kPa) at 40° C. 3-Nitrophenylacetonitrile (11 g), m.p. 60° C., is thereby obtained.

EXAMPLE 52

The procedure used is similar to that described in Example 49, but starting with 2-{2-[(1-imidazolyl)carboxamido]-N-(3-hydroxyphenyl)acetamido} -N-methyl-N-phenylacetamide (1.0 g) and 3-aminophenylmethanol (0.6 g). The crude product is purified by chromatography on silica (0.065–0.200 mm) (40 g) contained in a column 2 cm in diameter [eluent: ethanol/ethyl acetate (5:95 by volume)], collecting 10-cc fractions. Fractions 7 to 13 are combined and concentrated to dryness under reduced pressure (2.7 kPa) at 40° C. After recrystallisation in an ethyl acetate/diisopropyl ether (80:20 by volume) mixture, 2-[ 2-{3-[3-(hydroxymethyl)phenyl]ureido}-N-(3-hydroxyphenyl)acetamido] -N-methyl-N-phenylacetamide (0.2 g), m.p. 160° C., is obtained.

2-{2-[(1-Imidazolyl)carboxamido]-N-(3-hydroxyphenyl)acetamido} -N-methyl-N-phenylacetamide may be prepared in a manner similar to that described in Example 49 for the preparation of 2-{2-[(1-imidazolyl)carboxamido] -N-(3-methoxyphenyl)acetamido}-N-methyl-N-phenylacetamide, but starting with 2-[2-amino-N-(3-hydroxyphenyl)acetamido] -N-methyl-N-phenylacetamide (0.9 g) and N,N'-carbonyldiimidazole (0.7 g). 2-{2-[(1-Imidazolyl)carboxamido]-N-(3-hydroxyphenyl)acetamido} -N-methyl-N-phenylacetamide (0.9 g) is thereby obtained in the form of an oil, which is used without further purification in the subsequent syntheses.

2-[2-Amino-N-(3-hydroxyphenyl)acetamido]-N-methyl-N-phenylacetamide may be prepared in a manner similar to that described in Example 4 for the preparation of tert-butyl 2-[2-amino-N-(2-trifluoromethoxyphenyl)acetamido] acetate, but starting with 2-[N-(3-hydroxyphenyl)-2-phthalimidoacetamido]-N-methyl-N-phenylacetamide (2.0 g) and hydrazine hydrate (0.45 g). 2-[2-Amino-N-(3-hydroxyphenyl)acetamido]-N-methyl-N-phenylacetamide (0.9 g) is thereby obtained in the form of an oil, which is used without further purification in the subsequent syntheses.

2-[N-(3-Hydroxyphenyl)-2-phthalimidoacetamido] -N-methyl-N-phenylacetamide may be prepared in the following manner: a solution of 2-[N-(3-methoxyphenyl)-2 -phthalimidoacetamido]-N-methyl-N-phenylacetamide (2 g) in methylene chloride (20 cc) is added in the course of 10 minutes to a 1M solution (13.3 cc), maintained under a nitrogen atmosphere at a temperature in the region of –50° C., of boron tribromide in methylene chloride. The mixture obtained is stirred for 30 minutes at a temperature in the region of –50° C. and then 16 hours at a temperature in the region of 20° C. Water (25 cc) is then added, followed by methylene chloride (25 cc). The organic phase is separated after settling has taken place, washed with water (4×30 cc), dried over magnesium sulphate and concentrated to dryness under reduced pressure (2.7 kPa) at 40° C. 2-[N-(3-Hydroxyphenyl)-2-phthalimidoacetamido] -N-methyl-N-phenylacetamide (0.9 g) is thereby obtained in the form of an oil, which is used without further purification in the subsequent syntheses.

EXAMPLE 53

The procedure used is similar to that described in Example 1, but starting with 2-[2-amino-N-(3 -ethoxyphenyl)acetamido]-N-methyl-N-phenylacetamide (1.0 g) and 3-methylphenyl isocyanate (0.33 g). The crude product obtained is purified by chromatography on silica (0.065–0.200 mm) (40 g) contained in a column 2.0 cm in diameter [eluent: cyclohexane/ethyl acetate (30:70 by volume)], collecting 20-cc fractions. Fractions 5 to 13 are combined and concentrated to dryness under reduced pressure (2.7 kPa) at 40° C. After recrystallisation in an ethyl acetate/diisopropyl ether (10:90 by volume) mixture, 2-{N-(3-ethoxyphenyl)-2-[3-(3 -methylphenyl)ureido]acetamido}-N-methyl-N-phenylacetamide (0.3 g), m.p. 98° C., is obtained.

2-[2-Amino-N-(3-ethoxyphenyl)acetamido]-N-methyl-N-phenylacetamide may be prepared in a manner similar to that described in Example 4 for the preparation of tert-butyl 2-[2-amino-N-(2-trifluoromethoxyphenyl)acetamido] acetate, but starting with 2-[N-(3-ethoxyphenyl)-2-phthalimidoacetamido]-N-methyl-N-phenylacetamide (1.2 g) and hydrazine hydrate (0.28 g). 2-[2-Amino-N-(3-ethoxyphenyl)acetamido]-N-methyl-N-phenylacetamide (1 g) is thereby obtained in the form of an oil, which is used without further purification in the subsequent syntheses.

2-[N-(3-Ethoxyphenyl)-2-phthalimidoacetamido] -N-methyl-N-phenylacetamide may be prepared in the following manner: an oily suspension (50% by weight) (0.24 g) of sodium hydride is added at a temperature in the region of 10° C. to a solution of 2-[N-(3-hydroxyphenyl)-2-phthalimidoacetamido]-N-methyl-N-phenylacetamide (2.7 g) in N,N-dimethylformamide (15 cc). The suspension is stirred for 30 minutes at a temperature in the region of 10° C. and ethyl iodide (1.0 g) is then added. The mixture is stirred for 2 hours at a temperature in the region of 25° C. and then poured into a mixture of water (150 cc) and ethyl acetate (200 cc). The organic phase is separated after settling has taken place, washed with water (2×100 cc), dried over magnesium sulphate and concentrated to dryness under reduced pressure (2.7 kPa) at 35° C. The crude product is purified by chromatography on silica (0.063–0.2 mm) (50 g) contained in a column 2.5 cm in diameter [eluent: cyclohexane/ethyl acetate (40:60 by volume)], collecting 20-cc fractions. Fractions 4 to 7 are combined and concentrated to dryness under reduced pressure (2.7 kPa) at 40° C. 2-[N-(3-Ethoxyphenyl)-2-phthalimidoacetamido] -N-methyl-N-phenylacetamide (1.2 g) is thereby obtained in the form of an oil, which is used without further purification in the subsequent syntheses.

EXAMPLE 54

The procedure used is similar to that described in Example 1, but starting with 2-[2-amino-N-(3 -methoxyphenyl)acetamido]-N-(2-fluorophenyl)-N-methylacetamide (0.8 g) and 3-methylphenyl isocyanate (0.32 g). The product obtained is purified by chromatography on silica (0.065–0.200 mm) (40 g) contained in a column 2 cm in diameter [eluent: methylene chloride/ethanol (95:5 by volume)], collecting 20-cc fractions. Fractions 8 to 12 are combined and concentrated to dryness under reduced pressure (2.7 kPa) at 40° C. After recrystallisation in a diisopropyl ether/acetonitrile (90:10 by volume) mixture, N-[([2-fluorophenyl)-2-{N-(3-methoxyphenyl)-2-[ 3-(3-methylphenyl)ureido]acetamido}-N-methylacetamide (0.7 g), m.p. 110° C., is obtained.

2-[2-Amino-N-(3-methoxyphenyl)acetamido]-N-(2 -fluorophenyl)-N-methylacetamide may be prepared in a manner similar to that described in Example 4 for the preparation of tert-butyl 2-[2-amino-N-(2-trifluoromethoxyphenyl)acetamido] acetate, but starting with N-(2-fluorophenyl)-2-[N-(3-methoxyphenyl)-2-phthalimidoacetamido] -N-methylacetamide (6.2 g) and hydrazine hydrate (1.3 g). 2-[2-Amino-N-(3-methoxyphenyl)acetamido]-N-(2-fluorophenyl)-N-methylacetamide (4.0 g) is thereby obtained in the form of an oil, which is used without further purification in the subsequent syntheses.

N-(2-Fluorophenyl)-2-[N-(3-methoxyphenyl)-2-phthalimidoacetamido] -N-methylacetamide may be prepared in the following manner: oxalyl dichloride (3.5 g) and then dimethylformamide (0.2 cc) are added to a suspension of 2-[N-(3-methoxyphenyl)-2-phthalimidoacetamido] acetic acid (9.2 g) in 1,2-dichloroethane (150 cc). The mixture is stirred for 2 hours at a temperature in the region of 25° C. and 2-fluoro-N-methylaniline (3.1 g) and pyridine (2 g) dissolved in 1,2-dichloroethane (20 cc) are then added. The solution is stirred for 2 hours at a temperature in the region of 25° C. and then washed with water (2×100 cc). The organic phase is dried over magnesium sulphate and concentrated to dryness under reduced pressure (2.7 kPa) at 40° C. The crude product obtained is purified by chromatography on silica (0.065–0.200 mm) (80 g) contained in a column 4.0 cm in diameter [eluent: methylene chloride/methanol (98:2 by volume)], collecting 30-cc fractions. Fractions 5 to 13 are combined and concentrated to dryness under reduced pressure (2.7 kPa) at 40° C. N-(2-Fluorophenyl)-2-[N-(3 -methoxyphenyl)-2-phthalimidoacetamido]-N-methylacetamide (6.2 g) is thereby obtained in the form of a meringue-like product, which is used without further purification in the subsequent syntheses.

2-[N-(3-Methoxyphenyl)-2-phthalimidoacetamido] acetic acid may be prepared in the following manner: trifluoroacetic acid (32.9 g) is added to a solution of tert-butyl 2-[N-(3-methoxyphenyl)-2-phthalimidoacetamido] acetate (19 g) in dichloromethane (220 cc). The solution obtained is stirred under reflux for 4 hours and then concentrated to dryness under reduced pressure (2.7 kPa) at 40° C. After recrystallisation in diisopropyl ether, 2-[N-(3 -methoxyphenyl)-2-phthalimidoacetamido]acetic acid (16 g), m.p. 198° C., is obtained.

2-Fluoro-N-methylaniline may be prepared in the following manner: a solution of 2-fluoroformanilide (12.2 g) in anhydrous tetrahydrofuran (100 cc) is added in the course of 15 minutes to a suspension, maintained at a temperature in the region of 25° C., of lithium aluminium hydride (4.9 g) in anhydrous tetrahydrofuran (100 cc). The mixture is stirred at a temperature in the region of 25° C. for 3 hours. After cooling to a temperature in the region of 5° C., water (5.7 cc), 5N aqueous sodium hydroxide solution (4.2 cc) and then water (19 cc) are added successively. The suspension obtained is stirred for 30 minutes and diethyl ether (150 cc) is added. The insoluble product is separated by filtration and the filtrate is concentrated to dryness under reduced pressure (2.7 kPa) at 40° C. The residue is dissolved in dichloromethane (60 cc) and the solution is dried over magnesium sulphate and then concentrated to dryness under reduced pressure (2.7 kPa) at 40° C. 2-Fluoro-N-methylaniline (7.2 g) is thereby obtained in the form of an oil, which is used without further purification in the subsequent syntheses.

2-Fluoroformanilide may be prepared in the following manner: 2-fluoroaniline (11 g) is added to a solution of sodium methylate (10.8 g) in anhydrous dimethylformamide (100 cc). The mixture is heated to reflux for 2 hours, distilling off the methanol formed, and then concentrated to dryness under reduced pressure (0.01 kPa) at 60° C. The residue is taken up with water (1 liter) and diethyl ether (300 cc). The organic phase is separated after settling has taken place, dried over magnesium sulphate and concentrated to dryness under reduced pressure (2.7 kPa) at 30° C. 2-Fluoroformanilide (12.2 g) is thereby obtained in the form of an oil, which is used without further purification in the subsequent syntheses.

EXAMPLE 55

The procedure used is similar to that described in Example 26, but starting with ethyl 3-[3-{ N-[2-(3,4-dihydro-2H-1,4-benzothiazin-4-yl)-2-oxoethyl] -N-(3-methoxyphenyl)carbamoylmethyl}ureido]benzoate (3.1 g) and 1N aqueous sodium hydroxide solution (5.5 cc). 3-[3-{N-[2-(3,4-Dihydro-2H-1,4-benzothiazin-4 -yl)-2-oxoethyl] -N-(3-methoxyphenyl)carbamoylmethyl} ureido]benzoic acid (1.6 g), m.p. 165° C., is thereby obtained.

Ethyl 3-[3-{N-[2-(3,4-dihydro-2H-1,4-benzothiazin-4 -yl)-2-oxoethyl]-N-(3-methoxyphenyl)carbamoylmethyl} ureido]benzoate may be prepared in a manner similar to that described in Example 49 for the preparation of 2-[2-{3-[3-(2-hydroxyethyl)phenyl]ureido} -N-(3-methoxyphenyl)acetamido]]-N-methyl-N-phenylacetamide, but starting with N-[2-(3,4-dihydro-2 H-1,4-benzothiazin-4-yl)-2-oxoethyl]-2-[ (1-imidazolyl)carboxamido]-N-(3-methoxyphenyl)acetamide (3.0 g) and ethyl 3-aminobenzoate (2.2 g). The product obtained is purified by chromatography on silica (0.065–0.200 mm) (150 g) contained in a column 5 cm in diameter [eluent: methylene chloride/ethyl acetate (70:30 by volume)], collecting 30-cc fractions. Fractions 24 to 36 are combined and concentrated to dryness under reduced pressure (2.7 kPa) at 40° C. Ethyl 3-[3-{N-[2-(3,4-Dihydro-2H-1,4-benzothiazin-4-yl)-2-oxoethyl] -N-(3-methoxyphenyl)carbamoylmethyl}ureido]benzoate (3.2 g) is thereby obtained in the form of a meringue-like product, which is used without further purification in the subsequent syntheses.

N-[2-(3,4-Dihydro-2H-1,4-benzothiazin-4-yl)-2 -oxoethyl]-2-[(1-imidazolyl)carboxamido]-N-(3-methoxyphenyl)acetamide may be prepared in a manner similar to that described in Example 49 for the preparation of 2-{2-[(1-imidazolyl)carboxamido]-N-(3 -methoxyphenyl)acetamido}-N-methyl-N-phenylacetamide, but starting with 2-amino-N-[2-(3,4-dihydro-2H-1,4-benzothiazin-4 -yl)-2-oxoethyl]-N-(3-methoxyphenyl)acetamide (3.6 g) and N,N'-carbonyldimidazole [sic] (2.6 g). N-[2-(3,4-dihydro-2H-1,4-benzothiazin-4-yl)-2-oxoethyl] -2-[(1-imidazolyl)carboxamido]-N-(3-methoxyphenyl)acetamide (3.1 g) is thereby obtained in the form of an amorphous powder, which is used without further purification in the subsequent syntheses.

2-Amino-N-[2-(3,4-dihydro-2H-1,4-benzothiazin-4 -yl)-2-oxoethyl]-N-(3-methoxyphenyl)acetamide may be prepared in a manner similar to that described in Example 4 for the preparation of tert-butyl 2-[2-amino-N-(2-trifluoromethoxyphenyl)acetamido] acetate, but starting with N-[2-(3,4-dihydro-2 H-1,4-benzothiazin-4-yl)-2-oxoethyl]-N-(3-methoxyphenyl)-2 -phthalimidoacetamide (8.0 g) and hydrazine hydrate (1.6 g). 2-Amino-N-[2-(3,4-dihydro-2H-1,4-benzothiazin-4 -yl)-2-oxoethyl]-N-(3-methoxyphenyl)acetamide (5.9 g) is thereby obtained in the form of an oil, which is used without further purification in the subsequent syntheses.

N-[2-(3,4-Dihydro-2H-1,4-benzothiazin-4-yl)-2 -oxoethyl]-N-(3-methoxyphenyl)-2-phthalimidoacetamide may be prepared in a manner similar to that described in Example 54 for the preparation of N-(2-fluorophenyl)-2 -[N-(3-methoxyphenyl)-2-phthalimidoacetamido]-N-methylacetamide, but starting with 2-[N-(3-methoxyphenyl)-2 -phthalimidoacetamido]acetic acid (9.2 g), oxalyl dichloride (3.5 g), 3,4-dihydro-2H-1,4-benzothiazine (3.8 g) and pyridine (2 g). After recrystallisation in an acetonitrile/diisopropyl ether (35:65 by volume) mixture, N-[2-(3,4-dihydro-2H-1,4-benzothiazin-4 -yl)-2-oxoethyl-N-(3-methoxyphenyl)-2-phthalimidoacetamide (8.2 g), m.p. 150° C., is obtained.

3,4-Dihydro-2H-1,4-benzothiazine may be prepared according to the method described by C. C. J. CULVENOR et al., J. Chem. Soc., 278 (1949).

EXAMPLE 56

The procedure used is similar to that described in Example 26, but starting with ethyl 3-[3-{ N-(3-methoxyphenyl)-N-[2-(1,2,3,4-tetrahydro-1-quinolyl)-2 -oxoethyl] carbamoylmethyl}ureido]benzoate (0.7 g) and 1N aqueous sodium hydroxide solution (1.3 cc). 3-[3-{N-(3-Methoxyphenyl)-N-[2-(1,2,3,4-tetrahydro-1 -quinolyl)-2-oxoethyl] carbamoylmethyl}ureido] benzoic acid (0.2 g), m.p. 190° C., is thereby obtained.

Ethyl 3-[3-{N-(3-methoxyphenyl)-N-[2-(1,2,3,4-tetrahydro-1 -quinolyl)-2-oxoethyl]carbamoylmethyl} ureido]benzoate may be prepared in a manner similar to that described in Example 49 for the preparation of 2-[2-{3-[3-(2-hydroxyethyl)phenyl]ureido} -N-(3-methoxyphenyl)acetamido]-N-methyl-N-phenylacetamide, but starting with 2-[(1-imidazolyl)carboxamido] -N-(3-methoxyphenyl)-N-[2-(1,2,3,4-tetrahydro-1 -quinolyl)-2-oxoethyl]acetamide (1.2 g) and ethyl 3-aminobenzoate (0.85 g). The product obtained is purified by chromatography on silica (0.065–0.200 mm) (40 g) contained in a column 2 cm in diameter [eluent: methylene chloride/ethyl acetate (70:30 by volume)], collecting 20-cc fractions. Fractions 31 to 40 are combined and concentrated to dryness under reduced pressure (2.4 kPa) at 40° C. Ethyl 3-[3-{N-(3-methoxyphenyl)-N-[2 -(1,2,3,4-tetrahydro-1-quinolyl)-2-oxoethyl] carbamoylmetyl}ureido] benzoate [sic] (0.7 g) is thereby obtained in the form of a meringue-like product, which is used without further purification in the subsequent syntheses.

2-[(1-Imidazolyl)carboxamido]-N-(3-methoxyphenyl)-N-[ 2-(1,2,3,4-tetrahydro-1-quinolyl)-2-oxoethyl] acetamide may be prepared in a manner similar to that described in Example 49 for the preparation of 2-{2-[(1-imidazolyl)carboxamido]-N-(3-methoxyphenyl)acetamido} -N-methyl-N-phenylacetamide, but starting with 2-amino-N-(3-methoxyphenyl)-N-[2-(1,2,3,4-tetrahydro-1 -quinolyl)-2-oxoethyl]acetamide (5.0 g) and N,N'-carbonyldiimidazole (4.2 g). 2-[(1-Imidazolyl)carboxamido] -N-(3-methoxyphenyl)-N-[2-(1,2,3,4-tetrahydro-1 -quinolyl)-2-oxoethyl]acetamide (2.3 g) is thereby obtained in the form of a meringue-like product, which is used without further purification in the subsequent syntheses.

2-Amino-N-(3-methoxyphenyl)-N-[2-(1,2,3,4-tetrahydro-1 -quinolyl)-2-oxoethyl]acetamide may be prepared in a manner similar to that described in Example 4 for the preparation of tert-butyl 2-[2-amino-N-(2 -trifluoromethoxyphenyl)acetamido]acetate, but starting with N-(3-methoxyphenyl)-2-phthalimido-N-[2-(1,2,3,4-tetrahydro-1 -quinolyl)-2-oxoethyl]acetamide (8.5 g) and hydrazine hydrate (1.7 g). 2-Amino-N-(3 -methoxyphenyl)-N-[2-(1,2, 3,4-tetrahydro-1-quinolyl)-2-oxoethyl] acetamide (5 g) is thereby obtained in the form of an oil, which is used without further purification in the subsequent syntheses.

N-(3-Methoxyphenyl)-2-phthalimido-N-[2 -(1,2,3,4-tetrahydro-1-quinolyl)-2-oxoethyl]-acetamide may be prepared in a manner similar to that described in Example 54 for the preparation of N-(2-fluorophenyl)-2-[N-(3-methoxyphenyl)-2-phthalimidoacetamido] -N-methylacetamide, but starting with 2-[N-(3-methoxyphenyl)-2-phthalimidoacetamido]acetic acid (8.0 g), oxalyl dichloride (3.0 g), 1,2,3,4-tetrahydroquinoline (3.5 g) and pyridine (1.8 g). N-(3-Methoxyphenyl)-2-phthalimido-N-[2-(1,2,3,4-tetrahydro-1 -quinolyl)-2-oxoethyl]acetamide (8.8 g) is thereby obtained in the form of an oil, which is used without further purification in the subsequent syntheses.

The present invention also relates to medicinal products consisting of at least one compound of formula (I), in the pure state or in the form of a composition in which it is combined with any other pharmaceutically compatible product, which can be inert or physiologically active. The medicinal products according to the invention may be employed orally, parenterally, rectally or topically.

As solid compositions for oral administration, tablets, pills, powders (gelatin capsules, wafer capsules) or granules may be used. In these compositions, the active principle according to the invention is mixed with one or more inert diluents such as starch, cellulose, sucrose, lactose or silica. These compositions can also comprise substances other than diluents, e.g. one or more lubricants such as magnesium stearate or talc, a colouring, a coating (dragées) or a varnish.

As liquid compositions for oral administration, pharmaceutically acceptable solutions, suspensions, emulsions, syrups and elixirs, containing inert diluents such as water, ethanol, glycerol, vegetable oils or liquid paraffin, may be used. These compositions can comprise substances other than diluents, e.g. wetting products, sweeteners, thickeners, flavourings or stabilisers.

The sterile compositions for parenteral administration can preferably be solutions, aqueous or non-aqueous, suspensions or emulsions. As a solvent or vehicle, water, propylene glycol, a polyethylene glycol, vegetable oils, especially olive oil, injectable organic esters, e.g. ethyl oleate, or other suitable organic solvents may be employed. These compositions can also contain adjuvants, especially wetting agents, tonicity agents, emulsifiers, dispersants and stabilisers. The sterilisation can be carried out in several ways, e.g. by aseptic filtration, by incorporating sterilising agents in the composition, by irradiation or by heating. They may also be prepared in the form of sterile solid compositions which can be dissolved at the time of use in a sterile injectable medium.

The compositions for rectal administration are suppositories or rectal capsules which contain, apart from the active product, excipients such as cocoa butter, semi-synthetic glycerides or polyethylene glycols.

The compositions for topical administration can be, e.g., creams, ointments, lotions, eye washes, mouth washes, nasal drops or aerosols.

In human therapy, the compounds according to the invention are especially useful in the treatment and prevention of disorders linked to CCK and gastrin at nervous system and gastrointestinal system level. These compounds may hence be used in the treatment and prevention of psychoses, anxiety disorders, Parkinson's disease, tardive dyskinesia, irritable colon syndrome, acute pancreatitis, ulcers, disorders of intestinal motility and certain tumours of the lower oesophagus, colon and intestine, and as an agent for boosting the analgesic activity of narcotic and non-narcotic analgesic medicinal products and as an appetite regulator.

The doses depend on the effect sought, the treatment period and the administration route used; administered orally, they are generally between 0.05 g and 1 g per day for an adult, with single doses ranging from 10 mg to 500 mg of active substance.

Generally speaking, the attending physician will determine the appropriate dosage in accordance with the age, weight and all other factors specific to the subject to be treated.

The examples which follow illustrate compositions according to the invention:

EXAMPLE A

Hard gelatin capsules containing 50 mg of product and having the following composition are prepared according to the usual technique:

| | |
|---|---|
| 3-{3-[N-(3-methoxyphenyl)- N-(N-methyl-N-phenylcarbamoyl- methyl)carbamoylmethyl]ureido}- benzoic acid | 50 mg |
| cellulose | 18 mg |
| lactose | 55 mg |
| colloidal silica | 1 mg |
| carboxymethylstarch sodium | 10 mg |
| talc | 10 mg |
| magnesium stearate | 1 mg |

EXAMPLE B

Tablets containing 50 mg of active product and having the following composition are prepared according to the usual technique:

| | |
|---|---|
| tert-butyl 2-{N-[2-(3,3-dimethyl- piperidino)carbonylphenyl]-2- [3-(3-methylphenyl)ureido]- acetamido}acetate | 50 mg |
| lactose | 104 mg |
| cellulose | 40 mg |
| polyvidone | 10 mg |
| carboxymethylstarch sodium | 22 mg |
| talc | 10 mg |
| magnesium stearate | 2 mg |
| colloidal silica | 2 mg |
| mixture of hydroxymethylcellulose, glycerol and titanium oxide (72:3.5:24.5) | q.s. |
| 1 finished film-coated tablet weighing | 245 mg |

EXAMPLE C

An injectable solution containing 10 mg of active product and having the following composition is prepared:

| | |
|---|---|
| 3-{3-[N-(3-methoxyphenyl)-N-(N- methyl-N-phenylcarbamoylmethyl)- carbamoylmethyl]ureido}phenyl- acetic acid | 10 mg |
| benzoic acid | 80 mg |
| benzyl alcohol | 0.06 cc |
| sodium benzoate | 80 mg |
| ethanol, 95% | 0.4 cc |
| sodium hydroxide | 24 mg |
| propylene glycol | 1.6 cc |
| water. . . q.s. | 4 cc |

We claim:
1. A compound of the formula

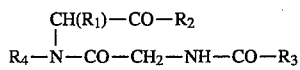

wherein $R_1$ is hydrogen, alkyl, alkoxycarbonyl, phenyl or phenyl substituted with at least one substituent selected from halogen, alkyl, alkoxy, alkylthio, nitro and amino, $R_2$ is (a) alkoxy, (Co) cycloalkyloxy, (c) cycloalkyloxy substituted with at least one alkyl, (d) cycloalkylalkyloxy, (e) phenylalkyloxy, (f) polyfluoroalkyloxy, (g) cinnamyloxy or (h) —$NR_5R_6$, $R_3$ is (a) phenylamino, (b) phenylamino wherein the phenyl is substituted with at least one substituent selected from halogen, alkyl, alkoxy, alkylthio, carboxyl, hydroxyl, mono- or polyhydroxyalkyl, nitro, amino, acyl, cyano, sulphamoyl, carbamoyl, benzoyl, trifluoromethylsulphonamido, alkoxycarbonyl, phenylhydroxymethyl, piperidino, hydroxyiminoalkyl, alkoxyiminoalkyl, alkylsulphinyl, hydroxyaminocarbonyl, alkoxyaminocarbonyl, 5-tetrazolyl, 5-tetrazolylalkyl, sulpho, —alk-O-CO-alk, —alk-O-alk, —alk-COOX, —O-alk-COOX, —alk'-COOX, —CH=CH-COOX, —CO-COOX, —alk-$SO_3H$, —CH=CH-alk', —C(=NOH)-COOX and —S-alk-COOX, (c) phenyl, (d) phenyl substituted with at least one substituent selected from halogen, alkyl, alkoxy and alkylthio, (e) naphthyl, (f) indolyl or (g) quinolyl, $R_4$ is phenyl substituted with at least one substituent selected from halogen atoms, alkyl, alkoxy, hydroxyl, polyfluoroalkyl, nitro, alkylthio, alkoxycarbonyl, carboxyl, acylamino, methylenedioxy, polyfluoroalkoxy, trifluoromethylthio, phenoxy, phenyl, benzyl, phenylamino and —CO-NR$_5$R$_6$, R$_5$ and R$_6$, which may be identical or different, are (a) hydrogen, (b) alkyl, (c) phenyl, (d) phenyl substituted with at least one substituent selected from halogen, alkyl, alkoxy and alkylthio, (e) indanyl, (f) cycloalkylalkyl, (g) cycloalkyl or (h) phenylalkyl, or alternatively R$_5$ and R$_6$, together with the nitrogen atom to which they are attached, form (a) a saturated or unsaturated mono- or polycyclic heterocycle containing 4 to 9 carbon atoms and at least one hetero atom selected from O, N, S, (b) a saturated or unsaturated mono- or polycyclic heterocycle containing 4 to 9 carbon atoms and at least one heteroatom selected from O, N, S substituted with at least one alkyl, alkoxy, alkoxycarbonyl, dialkylcarbamoyl, phenyl, 4- or 5-membered spiromonocyclic ring formed with a carbon atom of the heterocycle or 4- or 5-membered spiromonocyclic ring formed with a carbon atom of the heterocycle and containing at least one hetero atom selected from O, S, N, alk is alkyl or alkylene, alk' is hydroxyalkylene or hydroxyalkyl, X is hydrogen or alkyl, wherein the alkyl, alkylene and alkoxy radicals and alkyl, alkylene and alkoxy portions contain 1 to 4 carbon atoms in the straight or branched chain, and wherein the cycloalkyl radicals and portions contain 3 to 6 carbon atoms, wherein the acyl radicals contain 2 to 4 carbon atoms, as well as its racemates and its enantiomers when it contains at least one asymmetric centers.

2. A compound of the formula (I) according to claim 1 wherein R$_5$ and R$_6$, together with the nitrogen atom to which they are attached, form (a) piperidino, Co) piperidino substituted with at least one alkyl, phenyl, alkoxycarbonyl or dialkylcarbamoyl, (c) a perhydro-1-azepinyl, (d) 1-indolinyl, (e) 1,2,3,6-tetrahydro-1-pyridyl, (f) 1,2,3,4-tetrahydro-1-quinolyl, (g) 1-pyrrolidinyl, (h) 3,4-dihydro-2H- 1,4-benzoxazin-4-yl, (i) 3,4-dihydro-2H-1,4-benzothiazino 4-yl, (j) N-alkyl-1,2,3,4-tetrahydro-1-quinoxalinyl, (k)perhydro-1-quinolyl, (l) 1,2,3,4-tetrahydro-2-isoquinolyl, (m)8-azaspiro[4.5]decan-8-yl, (n)8-aza-1,4-dioxaspiro[4.5]decan-8-yl, (o) 2- or 3-phenyl-1-pyrrolidinyl, (p) thiomorpholino, (q) thiomorpholino substituted with at least one alkyl radical.

3. A compound of formula (I) according to claim 1, wherein the halogen atoms are chlorine, bromine or fluorine atoms.

4. A compound of formula (I) according to claim 1, wherein R$_1$ is hydrogen, R$_2$ is alkoxy or —NR$_5$R$_6$, R$_3$ is phenylamino in which the phenyl ring is substituted with at least one substituent selected from alkyl, monohydroxyalkyl, carboxyl and —alk-COOH and R$_4$ is phenyl substituted with at least one substituent selected from halogen, alkoxy, hydroxyl, alkoxycarbonyl and —CO-NR$_5$-R$_6$.

5. A pharmaceutical composition comprising as active principle at least one compound of formula (I) according to claim 1.

6. A pharmaceutical composition comprising as active principle at least one compound according to claim 2.

7. A pharmaceutical composition according to claim 5, for the treatment or prevention of disorders linked to CCK and gastrin at nervous system and gastrointestinal system level.

8. A pharmaceutical composition comprising as active principle at least one compound according to claim 3.

9. A pharmaceutical composition comprising as active principle at least one compound according to claim 4.

* * * * *

UNITED STATES PATENT AND TRADEMARK OFFICE
CERTIFICATE OF CORRECTION

PATENT NO. : 5,475,106
DATED : December 12, 1995
INVENTOR(S) : Jean-Dominique BOURZAT et al.

It is certified that error appears in the above-indentified patent and that said Letters Patent is hereby corrected as shown below:

In Claim 1, Column 50, line 43, "Co)" should read --(b)--.

In Claim 2, Column 51, line 33, "Co)" should read --(b)--.

In Claim 2, Column 52, line 5, "3,4-dihydro-2H-1,4-benzothiazino 4-yl" should read --3,4-dihydro-2H-1,4-benzothiazin-4-yl--.

Signed and Sealed this

Seventeenth Day of September, 1996

*Attest:*

BRUCE LEHMAN

*Attesting Officer*   Commissioner of Patents and Trademarks